United States Patent
Chen et al.

(10) Patent No.: US 10,023,594 B2
(45) Date of Patent: Jul. 17, 2018

(54) ZWITTERIONIC ZINC(II) CARBOXYLATE COMPOUNDS AND THEIR USE

(71) Applicants: Southern Medical University, Guangzhou (CN); Macau University of Science and Technology, Taipa (MO)

(72) Inventors: Jin-Xiang Chen, Taipa (MO); Bin Sun, Taipa (MO); Hai-Qing Zhao, Taipa (MO); Bao-Ping Xie, Taipa (MO); Li-Ping Bai, Taipa (MO); Zhi-Hong Jiang, Taipa (MO)

(73) Assignees: MACAU UNIVERSITY OF SCIENCE AND TECHNOLOGY, Taipa (MO); SOUTHERN MEDICAL UNIVERSITY, Guangzhou (CN)

( * ) Notice: Subject to any disclaimer, the term of this patent is extended or adjusted under 35 U.S.C. 154(b) by 0 days.

(21) Appl. No.: 15/251,300

(22) Filed: Aug. 30, 2016

(65) Prior Publication Data

US 2018/0057512 A1    Mar. 1, 2018

(51) Int. Cl.
*C07F 3/06* (2006.01)
*C12Q 1/70* (2006.01)

(52) U.S. Cl.
CPC ............... *C07F 3/06* (2013.01); *C12Q 1/703* (2013.01)

(58) Field of Classification Search
CPC ....................................................... C07F 3/06
USPC ............................................................ 546/2
See application file for complete search history.

(56) References Cited

PUBLICATIONS

Chen et al. The Royal Society of Chemistry 2015 Dalton Trans., 2015, 44, 13369-13377.*
Chen et al. Polyhedron (1994), 13(13), 2079-83.*
Chen JX, Lin WE, Zhou CQ, et al. Synthesis, crystal structures and biological evaluation of water-soluble zinc complexes of zwitterionic carboxylates. Inorg Chim Acta. 2011;376(1):389-95.
Chen M, Chen MZ, Zhou CQ, et al. Towards polynuclear metal complexes with enhanced bioactivities: Synthesis, crystal structures and DNA cleaving activities of Cu(II), Ni(II), Zn(II), Co(II) and Mn(II) complexes derived from 4-carboxy-1-(4-carboxybenzyl) pyridinium bromide. Inorg Chim Acta. 2013;405:461-9.
Chen JX, Lin WE, Chen M, et al. Synthesis and DNA photocleaving activities of ancillary ligand-containing zinc complexes of quaternized carboxylates. Inorg Chim Acta. 2014;409:195-201.
Chen M, Tang XY, Yang SP, et al. Five water-soluble zwitterionic copper(II)-carboxylate polymers: role of dipyridyl coligands in enhancing the DNA-binding, cleaving and anticancer activities. Dalton transactions. 2015;44(29):13369-77.
Farrugia LJ. WinGX suite for small molecule single-crystal crystallography. J Appl Cryst. 1999;32:837-8.
Liu D, Li HX, Liu LL, et al. How do substituent groups in the 5-position of 1,3-benzenedicarboxylate affect the construction of supramolecular frameworks? CrystEngComm. 2010;12(11):3708-16.
Liu D, Ren ZG, Li HX, et al. pH-dependent solvothermal formation of two different 3D multiple interpenetrating nets from the same components of Zn(NO3)2,1,3-benzenedicarboxylate and 1,4-bis[2-(4-pyridyl)ethenyl]benzene. CrystEngComm. 2010;12:1912-9.
Morris W, Briley WE, Auyeung E, et al. Nucleic acid-metal organic framework (MOF) nanoparticle conjugates. J Am Chem Soc. 2014;136(20):7261-4.
Huxley AJ, Schroeder M, Gunaratne HQ, de Silva AP. Modification of fluorescent photoinduced electron transfer (PET) sensors/switches to produce molecular photo-ionic triode action. Angew Chem Int Ed Engl. 2014;53(14):3622-5.
Gnapareddy B, Ahn SJ, Dugasani SR, et al. Coverage percentage and raman measurement of cross-tile and scaffold cross-tile based DNA nanostructures. Colloids and surfaces B: Biointerfaces. 2015;135:677-81.
Kannan B., Williams D.E., Booth M.A., Travas-Sejdic J., "High-sensitivity, label-free DNA sensors using electrochemically active conducting polymers", Anal. Chem. 201, 83(9), pp. 3415-3421.
Soontornworajit B., Wang Y., "Nucleic acid aptamers for clinical diagnosis: cell detection and molecular imaging. Analytical and bioanalytical chemistry", 2011, 399(4), pp. 1591-1599.
Larguinho M., Baptista P.V., "Gold and silver nanoparticles for clinical diagnostics—From genomics to proteomics", J. Proteomics, 2012, 75(10), pp. 2811-2823.
Lu C.H., Yang H.H., Zhu C.L., et al., "A graphene platform for sensing biomolecules", Angew Chem. Int. Ed. Engl., 2009, 48(26), pp. 4785-4787.
Wen Y., Xing F., He S., et al., "A graphene-based fluorescent nanoprobe for silver(I) ions detection by using graphene oxide and a silver-specific oligonucleotide", Chem. Commun. (Camb.), 2010, 46(15), pp. 2596-2598.

(Continued)

*Primary Examiner* — Nizal S Chandrakumar
(74) *Attorney, Agent, or Firm* — Renner Kenner Greive Bobak Taylor & Weber

(57) ABSTRACT

A method of preparing a crystalline zwitterionic zinc(II)-carboxylate compound includes the steps of preparing a mixture of zinc(II) ions and a first pyridyl ligand having three carboxylic acid moieties; subjecting the mixture to conditions under which a precipitate is formed; separating the precipitate; adding a solvent and optionally a second pyridyl ligand to the separated precipitate; subjecting the obtained mixture to conditions under which crystals of the zwitterionic zinc(II)-carboxylate compound are formed; and separating the crystals of the zwitterionic zinc(II)-carboxylate compound. Preferably but not exclusively, the crystalline zwitterionic zinc(II)-carboxylate compound essentially consists of at least one 1D coordination polymer. The compounds are suitable for providing a sensing platform for detecting the presence or amount of target nucleic acid, particularly HIV-1 ds-DNA, with specificity, and, thus, a method of detecting a target nucleic acid sequence in a sample and a kit including the compounds and an oligonucleotide probe are also provided.

14 Claims, 15 Drawing Sheets
(6 of 15 Drawing Sheet(s) Filed in Color)

(56) References Cited

PUBLICATIONS

Yoo L., Ahn K.Y., Ahn J.Y., et al., "A simple one-step assay platform based on fluorescence quenching of macroporous silicon", Biosens. Bioelectron., 2013, 41, pp. 477-483.

Yang R., Jin J., Chen Y., et al., "Carbon nanotube-quenched fluorescent oligonucleotides: Probes that fluoresce upon hybridization", J. Am. Chem. Soc., 2008, 130(26), pp. 8351-8358.

Li H., Zhang Y., Luo Y., Sun X., "Nano-C(60) : a novel, effective, fluorescent sensing platform for biomolecular detection", Small., 2011, 7(11), pp. 1562-1568.

Sun C.Y., Qin C., Wang C.G., et al., "Chiral nanoporous metal-organic frameworks with high porosity as materials for drug delivery", Adv. Mater., 2011, 23(47), pp. 5629-5632.

He C., Lu K., Liu D., Lin W., "Nanoscale metal-organic frameworks for the co-delivery of cisplatin and pooled siRNAs to enhance therapeutic efficacy in drug-resistant ovarian cancer cells", J. Am. Chem. Soc., 2014, 136(14), pp. 5181-5184.

Huxford R.C., Della Rocca J., Lin W., "Metal-organic frameworks as potential drug carriers", Curr. Opin. Chem. Biol., 2010, 14(2), pp. 262-268.

Qin J.S., Du D.Y. Li W.L., et al., "N-rich zeolite-like metal-organic framework with sodalite topology: high CO2 uptake, selective gas adsorption and efficient drug delivery", Chemical Science, 2012, 3(6), pp. 2114-2118.

Bonnet C.S., Caille F., Pallier A., et al., "Mechanistic studies of Gd3+-based MRI contrast agents for Zn2+ detection: towards rational design", Chem. Eur. J. 2014, 20(35), pp. 10959-10969.

Taylor K.M., Kim J.S., Rieter W.J., et al., "Mesoporous silica nanospheres as highly efficient MRI contrast agents", J. Am. Chem. Soc., 2008, 130(7), pp. 2154-2155.

Taylor K.M., Rieter W.J., Lin W., "Manganese-based nanoscale metal-organic frameworks for magnetic resonance imaging", J. Am. Chem. Soc., 2008, 130(44), pp. 14358-14359.

Rieter W.J., Taylor K.M., An H., Lin W., Lin W., "Nanoscale metal-organic frameworks as potential multimodal contrast enhancing agents", J. Am. Chem. Soc., 2006, 128(28), pp. 9024-9025.

Banerjee R., Phan A., Wang B., et al., "High-throughput synthesis of zeolitic imidazolate frameworks and application to CO2 capture", Science, 2008, 319(5865), pp. 939-943.

Mueller U., Schubert M., Teich F., et al. "Metal-organic frameworks-prospective industrial applications", J. Mater. Chem., 2006, 16(7), pp. 626-636.

Yang C.X., Yan X.P., "Metal-organic framework MIL-101(Cr) for high-performance liquid chromatographic separation of substituted aromatics", Anal. Chem., 2011, 83(18), pp. 7144-7150.

Gu Z.Y., Wang G., Yan X.P., "MOF-5 metal-organic framework as sorbent for in-field sampling and preconcentration in combination with thermal desorption GC/MS for determination of atmospheric formaldehyde", Anal. Chem., 2010, 82(4), pp. 1365-1370.

Ni Z., Jerrell J.P., Cadwallader K.R., Masel, R.I., "Metal-organic frameworks as adsorbents for trapping and preconcentration of organic phosphonates", Anal. Chem., 2007, 79(4), pp. 1290-1293.

Liu D., Ren Z.G., Li H.X., et al., "Single-crystal-to-single-crystal transformations of two three-dimensional coordination polymers through regioselective [2+2] photodimerization reactions", Angew. Chem. Int. Ed. Engl., 2010, 49(28), pp. 4767-4770.

Liu D., Wang H.F., Abrahams B.F., Lang J.P., "Single-crystal-to-single-crystal transformation of a two-dimensional coordination polymer through highly selective [2+2] photodimerization of a conjugated dialkene", Chem. Commun. (Camb.), 2014, 50(24), pp. 3173-3175.

Liu W., Jiao T., Li Y., et al., "Lanthanide coordination polymers and their Ag+-modulated fluorescence", J. Am. Chem. Soc., 2004, 126(8), pp. 2280-2281.

Sezen B., Sames D., "Oxidative C-arylation of free (NH)-heterocycles via direct (sp3) C-H bond functionalization", J. Am. Chem. Soc., 2004, 126, 13244-13246, J. Am. Chem. Soc., 2006, 128(9), p. 3102.

Lefebvre J., Batchelor R.J., Leznoff D.B., "Cu[Au(CN)2]2(DMSO)2: golden polymorphs that exhibit vapochromic behavior", J. Am. Chem. Soc., 2004, 126(49), pp. 16117-16125.

Chen B., Wang L., Zapata F., et al., "A luminescent microporous metal-organic framework for the recognition and sensing of anions", J. Am. Chem. Soc., 2008, 130(21), pp. 6718-6719.

Bauer C.A., Timofeeva T.V., Settersten T.B., et al., "Influence of connectivity and porosity on ligand-based luminescence in zinc metal-organic frameworks", J. Am. Chem. Soc., 2007, 129(22), pp. 7136-7144.

Lu G., Hupp J.T., "Metal-organic frameworks as sensors: a ZIF-8 based Fabry-Perot device as a selective sensor for chemical vapors and gases", J. Am. Chem. Soc., 2010, 132(23), pp. 7832-7833.

Kreno L.E., Hupp J.T., Van Duyne R.P., "Metal-organic framework thin film for enhanced localized surface plasmon resonance gas sensing", Anal. Chem., 2010, 82(19), pp. 8042-8046.

Lee E.Y., Jang S.Y., Suh M.P., "Multifunctionality and crystal dynamics of a highly stable, porous metal-organic framework [Zn4O(NTB)2]", J. Am. Chem. Soc., 2005, 127(17), pp. 6374-6381.

Chen B., Yang Y., Zapata F., et al.,"Luminescent Open Metal Sites within a Metal-Organic Framework for Sensing Small Molecules", Adv. Mater., 2007, 19(13), pp. 1693-1696.

Zhu X., Zheng H., Wei X., et al., "Metal-organic framework (MOF): a novel sensing platform for biomolecules", Chem. Commun. (Camb.), 2013, 49(13), pp. 1276-1278.

Chen L., Zheng H., Zhu X., Lin Z., et al., "Metal-organic frameworks-based biosensor for sequence-specific recognition of double-stranded DNA", Analyst., 2013, 138(12), pp. 3490-3493.

Fang J.M., Leng F., Zhao X.J., et al., "Metal-organic framework MIL-101 as a low background signal platform for label-free DNA detection", Analyst., 2014, 139(4), pp. 801-806.

Guo J.F., Li C.M., Hu X.L., et al., "Metal-organic framework MIL-101 enhanced fluorescence anisotropy for sensitive detection of DNA", RSC Advances., 2014, 4(18), pp. 9379-9382.

Wang G.Y., Song C., Kong D.M., et al., "Two luminescent metal-organic frameworks for the sensing of nitroaromatic explosives and DNA strands", J. Mater. Chem. A., 2014, 2(7), pp. 2213-2220.

Zhang H.T., Zhang J.W., Huang G., et al., "An amine-functionalized metal-organic framework as a sensing platform for DNA detection", Chem. Commun. (Camb.), 2014, 50(81), pp. 12069-12072.

Yang S.P., Chen S.R., Liu S.W., et al., "Platforms Formed from a Three-Dimensional Cu-Based Zwitterionic Metal-Organic Framework and Probe ss-DNA: Selective Fluorescent Biosensors for Human Immunodeficiency Virus 1 ds-DNA and Sudan Virus RNA Sequences", Anal. Chem., 2015, 87(24), pp. 12206-12214.

Qin L., Lin L.X., Fang Z.P., et al., "A water-stable metal-organic framework of a zwitterionic carboxylate with dysprosium: a sensing platform for Ebolavirus RNA sequences", Chem. Commun. (Camb. ), 2016, 52(1), pp. 132-135.

Zhao C., Wu L., Ren J., et al., "Targeting human telomeric higher-order DNA: dimeric G-quadruplex units serve as preferred binding site", J. Am. Chem. Soc., 2013, 135(50), pp. 18786-18789.

Greathouse J.A., Allendorf M.D., "The interaction of water with MOF-5 simulated by molecular dynamics", J. Am. Chem. Soc., 2006, 128(33), pp. 10678-10679.

Zhang J.W., Zhang H.T., Du Z.Y., et al., "Water-stable metal-organic frameworks with intrinsic peroxidase-like catalytic activity as a colorimetric biosensing platform", Chem. Commun. (Camb.), 2014, 50(9), pp. 1092-1094.

Zheng J., Wu M., Jiang F., et al., "Stable porphyrin Zr and Hf metal-organic frameworks featuring 2.5 nm cages: high surface areas, SCSC transformations and catalyses", Chem. Sci., 2015, 6, pp. 3466-3470.

Chen J.X., Lin W.E., Chen M.Z., et al., "Synthesis, characterization and potent DNA-cleaving activity of copper(II)-complexed berberine carboxylate", Bioorg. Med. Chem. Lett., 2012, 22(23), pp. 7056-7059.

Chen M.Z., Chen M. Zhou C.Q., et al., "Synthesis, crystal structures and DNA-cleaving activities of [Cemp]2[MCl4] (Cemp = N-carbethoxymethyl-1,10-phenanthrolinium, M = Cu(II), Zn(II), Co(II), Ni(II) and Mn(II))", Chem. Pharm. Bull. (Tokyo), 2013, 61(7), pp. 714-721.

(56) References Cited

OTHER PUBLICATIONS

Wang Y.M. Zhou C.Q., Chen J.X., et al., "Facile synthesis of a polyether-tethered dimeric berberine as a highly effective DNA-cleaving agent in the presence of Cu(II) ion", MedChemComm. 2013, 4(10), pp. 1400-1404.

Vasylyeva V., Nayak S.K., Terraneo G., et al., "Orthogonal halogen and hydrogen bonds involving a peptide bond model. CrystEngComm", 2014, 16(35), pp. 8102-8105.

Zhang Z.X., Ding N.N., Zhang W.H., et al., "Stitching 2D polymeric layers into flexible interpenetrated metal-organic frameworks within single crystals", Angew Chem. Int. Ed. Engl. 2014, 53(18), pp. 4628-4632.

Chen J.X., Chen M., Ding N.N., et al., "Transmetalation of a dodecahedral Na9 aggregate-based polymer: a facile route to water stable Cu(II) coordination networks", Inorg. Chem., 2014, 53(14), pp. 7446-7454.

\* cited by examiner

SEQUENCE LISTING

<160> NUMBER OF SEQ ID NOS: 8

<210> SEQ ID NO 1
<211> LENGTH: 14
<212> TYPE: DNA
<213> ORGANISM: Artificial Sequence
<220> FEATURE:
<223> OTHER INFORMATION: DNA strand

<400> SEQUENCE: 1
ttcttctttt ttct                                                    14

<210> SEQ ID NO 2
<211> LENGTH: 26
<212> TYPE: DNA
<213> ORGANISM: Human immunodeficiency virus type 1

<400> SEQUENCE: 2
cgagttaaga agaaaaaaga ttgagc                                       26

<210> SEQ ID NO 3
<211> LENGTH: 26
<212> TYPE: DNA
<213> ORGANISM: Human immunodeficiency virus type 1

<400> SEQUENCE: 3
gctcaatctt tttcttctt aactcg                                        26

<210> SEQ ID NO 4
<211> LENGTH: 26
<212> TYPE: DNA
<213> ORGANISM: Artificial Sequence
<220> FEATURE:
<223> OTHER INFORMATION: DNA strand

<400> SEQUENCE: 4
cgagttaaga aaaaaaaga ttgagc                                        26

<210> SEQ ID NO 5
<211> LENGTH: 26
<212> TYPE: DNA
<213> ORGANISM: Artificial Sequence
<220> FEATURE:
<223> OTHER INFORMATION: DNA strand

<400> SEQUENCE: 5
gctcaatctt tttttttctt aactcg                                       26

<210> SEQ ID NO 6
<211> LENGTH: 14
<212> TYPE: DNA

```
<213> ORGANISM: Artificial Sequence
<220> FEATURE:
<223> OTHER INFORMATION: DNA strand

<400> SEQUENCE: 6
agaaaaaaga agaa                                                            14

<210> SEQ ID NO 7
<211> LENGTH: 14
<212> TYPE: DNA
<213> ORGANISM: Artificial Sequence
<220> FEATURE:
<223> OTHER INFORMATION: DNA strand

<400> SEQUENCE: 7
agaacaaaga agaa                                                            14

<210> SEQ ID NO 8
<211> LENGTH: 23
<212> TYPE: DNA
<213> ORGANISM: Artificial Sequence
<220> FEATURE:
<223> OTHER INFORMATION: DNA strand

<400> SEQUENCE: 8
gctagagatt ttccacactg act                                                  23
```

ZWITTERIONIC ZINC(II) CARBOXYLATE COMPOUNDS AND THEIR USE

SEQUENCE LISTING

The Sequence Listing file entitled "Sequence-ListingHFP07827" having a size of 1,658 bytes and creation date of 29 Aug. 2016 that was electronically filed with the patent application is incorporated herein by reference in its entirety.

TECHNICAL FIELD

The present invention relates to a method of preparing a crystalline zwitterionic zinc(II)-carboxylate compound and the crystalline zwitterionic zinc(II)-carboxylate compound obtained or obtainable by said method. Preferably but not exclusively, the crystalline zwitterionic zinc(II)-carboxylate compound comprises and in particular essentially consists of at least one 1D coordination polymer, i.e. with a 1D sheet-like network. Still further, the present invention provides a method of detecting a target nucleic acid sequence in a sample. The target nucleic acid sequence is in particular from a viral DNA or RNA, in particular proviral HIV-1 ds-DNA. Further provided is a kit comprising the crystalline zwitterionic zinc(II)-carboxylate compound and an oligonucleotide probe and its use.

BACKGROUND OF INVENTION

The detection of target DNA based on a quenching mechanism with fluorescently-labeled probe single-stranded (ss)-DNA has recently emerged as a powerful and extensively applied strategy due to its enormous applications in clinical diagnosis and the therapeutic field (Sassolas, A. et al., DNA biosensors and microarrays. Chem Rev. 2008; 108(1): 109-39, Kannan, B. et al., High-sensitivity, label-free DNA sensors using electrochemically active conducting polymers. Anal Chem. 2011; 83(9): 3415-21). Numerous materials have been employed as quenching platforms for labeled probe DNA for the determination of target DNA or RNA, including graphene oxide, macro-porous silicon and carbon nanomaterials. Although these materials function well to assay target DNA or RNA, their preparation is often complicated, time-consuming and expensive. As a consequence, further sensing platforms made from easily accessible materials are urgently required.

Owing to the advantage of easily obtained raw materials, mild reaction conditions and convenient preparation procedures, as well as their variety of configurations, metal-organic frameworks (MOFs) have increasingly attracted the interest of chemists and biologists and have been successfully applied in many fields of biomedicines, such as drug delivery, magnetic resonance imaging and others. In addition, MOFs have also been used in the detection of various cations, anions, vapors and other small molecules.

Recently, MOFs have been reported as sensing platforms for biomolecules, such as proteins, nucleic acids, antibodies and G quadruplexes (e.g. Zhu, X. et al., Metal-organic framework (MOF): a novel sensing platform for biomolecules. Chem Commun (Camb). 2013; 49(13): 1276-8, Chen, L. et al., Metal-organic frameworks-based biosensor for sequence-specific recognition of double-stranded DNA. Analyst. 2013; 138(12): 3490-3, Fang, J. M. et al, Metal-organic framework MIL-101 as a low background signal platform for label-free DNA detection. Analyst. 2014; 139 (4): 801-6, Zhang, H.T. et al., An amine-functionalized metal-organic framework as a sensing platform for DNA detection. Chem Commun (Camb). 2014; 50(81): 12069-72). This may rely on the fact that the organic linkers in MOFs usually have conjugated π-electron systems, which makes it possible to form π-π stacking with nucleic acid sequences. However, such development is still at its infant stage because of the poor water stability of most reported MOFs (Greathouse, J. A. and Allendorf, M. D., The interaction of water with MOF-5 simulated by molecular dynamics. J Am Chem Soc. 2006; 128(33): 10678-9, Zhang, J. W. et al., Water-stable metal-organic frameworks with intrinsic peroxidase-like catalytic activity as a colorimetric biosensing platform. Chem Commun (Camb). 2014; 50(9): 1092-4, Zheng, J. et al., Stable porphyrin Zr and Hf metal-organic frameworks featuring 2.5 nm cages: high surface areas, SCSC transformations and catalyses. Chem Sci. 2015; 6: 3466-70).

Accordingly, there remains a strong need for improved compounds which are easily obtainable in an economic way with sufficient water stability and sufficient DNA or RNA binding ability which are suitable to form sensing platforms for target DNA or RNA such as in the diagnosis of viral infectious diseases and in particular HIV infections.

SUMMARY OF THE INVENTION

The first aspect of the present invention relates to a method of preparing a crystalline zwitterionic zinc(II)-carboxylate compound.

Namely the method of the present invention comprises steps of:

(i) preparing a mixture comprising zinc(II) ions and a first pyridyl ligand which first pyridyl ligand is a zwitterionic pyridyl ligand having three carboxylic acid moieties, which mixture in particular further comprises nitrate ($NO_3^-$) ions;

(ii) subjecting the mixture to conditions under which a precipitate is formed and separating the precipitate;

(iii) adding a solvent and optionally a second pyridyl ligand to the separated precipitate and subjecting the obtained mixture to conditions under which crystals of the zwitterionic zinc(II)-carboxylate compound are formed; and (iv) separating the crystals of the zwitterionic zinc(II)-carboxylate compound.

The first pyridyl ligand in particular has a structure of Formula (I):

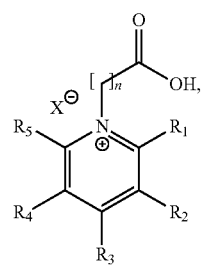

Formula (I)

wherein X is a halogen, preferably X is selected from Br, Cl or I. n is an integer and selected from 0, 1, 2 or 3. Two of $R^1$ to $R^5$ are a group of Formula (II):

Formula (II)

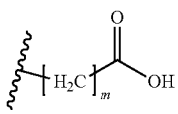

with m being an integer and selected from 0, 1 or 2 and the other of $R^1$ to $R^5$ being hydrogen.

In particular, the first pyridyl ligand has a structure of Formula (III):

Formula (III)

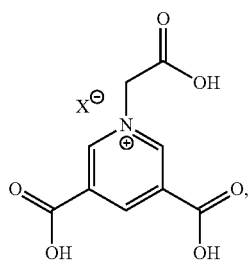

with X being as defined above. Preferably X is selected from Br, Cl or I, more preferably X is Br.

Step (iii) in particular comprises adding the second pyridyl ligand, which second pyridyl ligand has in particular a structure selected from Formula (IV), (V) or (VI):

Formula (IV)

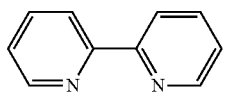

Formula (V)

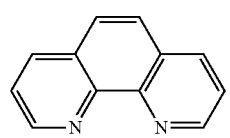

Formula (VI)

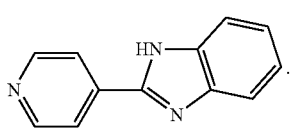

In particular embodiments of the present invention, the first pyridyl ligand has a structure of Formula (III) with X being Br and the second pyridyl ligand added in step (iii) has a structure of formula (IV).

The present invention further refers to the crystalline zwitterionic zinc(II)-carboxylate compound obtained or obtainable by the method described above, in particular obtained or obtainable by the method described above in which the first pyridyl ligand has a structure of Formula (III):

Formula (III)

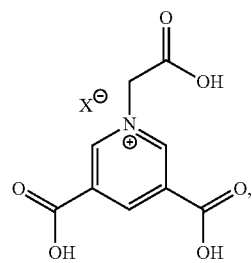

with X being Br and the second pyridyl ligand added in step (iii) has a structure of Formula (IV):

Formula (IV)

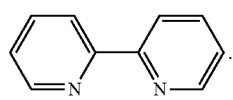

Still further, the present invention provides a method of detecting a target nucleic acid sequence in a sample. The target nucleic acid sequence is in particular from a viral or proviral DNA or RNA, most preferably HIV-1 double-stranded (ds)-DNA. The method comprises:

(i) preparing a mixture of a crystalline zwitterionic zinc (II)-carboxylate compound obtained or obtainable by the preparation method described above and an oligonucleotide probe having a nucleic acid sequence complementary to said target nucleic acid sequence and being labeled with a fluorescent;

(ii) incubating the mixture with the sample;

(iii) measuring the fluorescence after step (ii); and (iv) determining the presence and/or amount of the target nucleic acid sequence in the sample based on the fluorescence, which may optionally comprise a step of comparing the fluorescence measured in step (iii) with of at least one reference value such as the fluorescence of a reference sample without and/or at least one reference sample with a predetermined amount of target nucleic acid sequence.

In particular embodiments of the present invention, the crystalline zwitterionic zinc(II)-carboxylate compound used in step (i) of the method of detecting a target nucleic acid sequence in a sample is obtained or obtainable by the preparation method described above in which the first pyridyl ligand has a structure of Formula (III):

Formula (III)

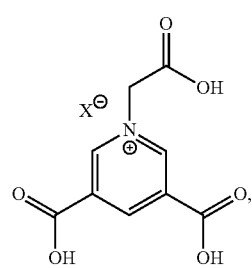

with X being Br and the second pyridyl ligand added in step (iii) has a structure of Formula (IV):

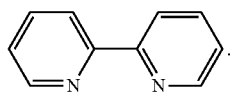

Formula (IV)

The oligonucleotide probe is in particular a carboxyfluorescein (FAM)-labeled ss-DNA sequence of SEQ. ID. NO: 1.

The method of the present invention of preparing a crystalline zwitterionic zinc(II)-carboxylate compound allows for preparing respective compounds with easily available starting materials, under mild reaction conditions and in a cost-efficient, fast and economic way. The obtained compounds bearing conjugated π electron systems with improved π-π interactions possess an exceptional water-stability and DNA-binding ability. They are especially suitable as biosensors and selective sensing platforms for the detection of virus or proviral DNA and RNA sequences in vitro by means of a fluorescently-labeled probe.

In particular, the crystalline zwitterionic zinc(II)-carboxylate compound which can be described by the formula $\{[Zn_2(Cmdcp)(bipy)_2(H_2O)_5](NO_3)_2 \cdot 3H_2O\}_n$ (also referenced as compound 2), wherein n means that the coordination entity $\{[Zn_2(Cmdcp)(bipy)_2(H_2O)_5](NO_3)_2 \cdot 3H_2O\}$ is repeated n times which will be understood by one of skill in the art, proved to be especially advantageous for detecting HIV-1 ds-DNA. It proved to be able to exceptionally bind to a FAM-labeled ss-DNA probe representing an effective fluorescent sensing platform for the detection of HIV-1 ds-DNA with a detection limit of 7.4 nM and with high selectivity. Compound 2, thus, proved to be especially suitable in the early diagnosis of HIV infections. Likewise it can be used in the diagnosis of other virus associated infectious diseases, such as Ebola, Dengue and the like.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 5A is a PXRD pattern of compound 1. FIG. 5B is a PXRD pattern of compound 2. FIG. 5C is a PXRD pattern of compound 4.

DETAILED DESCRIPTION OF INVENTION

Figure 1A:
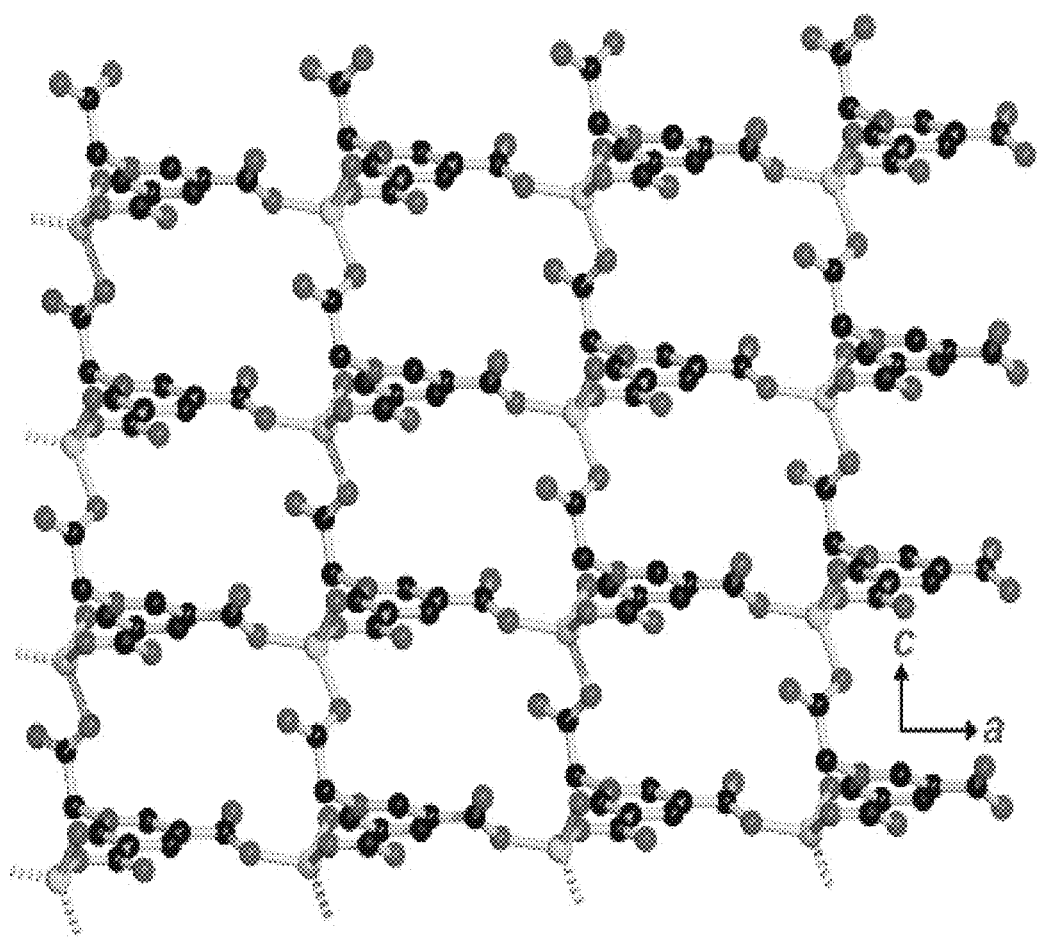
FIG. 1A shows the extended two-dimensional network structure of compound 1, i.e. a 2D coordination polymer which can be described with the formula $[Zn(Cmdcp)(H_2O)]_n$.

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element.

The present invention provides a method of preparing a crystalline zwitterionic zinc(II)-carboxylate compound.

Said term "zwitterionic zinc(II)-carboxylate compound" refers to a compound comprising and in particular essentially consisting of zwitterionic zinc(II)-carboxylate coordination entities. A "coordination entity" possesses the zinc(II) as the central atom which binds other atoms of groups or components referenced as ligands, thereby usually occupying a central position in said coordination entity. Ligands refers to the components or groups with atoms bound to the zinc(II). A coordination entity can comprise two or more zinc(II) central atoms. Preferably, the crystalline zwitterionic zinc(II)-carboxylate compound comprises and in particular essentially consists of one or more of either 1D coordination polymers or 2D coordination polymers. A 1D coordination polymer comprises repeating coordination entities extending in one dimension (1D). A 2D coordination polymer comprises repeating coordination entities extending in two dimensions (2D). Alternatively, the crystalline zwitterionic zinc(II)-carboxylate compound may comprise and in particular essentially consist of coordination entities in form of either cations or anions and respective counterions.

The expression "essentially consisting of" in relation to the zwitterionic zinc(II)-carboxylate compound does not exclude that further ions, in particular anions such as $NO_3^-$ ions from the preparation process are still present in the compound, for example, in order to balance positive charges of the coordination entities.

The zwitterionic zinc(II)-carboxylate compound prepared according to the method of the present invention is crystalline, which shall mean that the atoms or molecules are substantially organized in a structure known as a crystal. Said term is generally used in the art for any structure of ions, molecules, or atoms that are held together in an ordered arrangement. A crystalline structure is one of two types of structural ordering of atoms, ions or molecules the other being the amorphous structure which is irregular and lacks an orderly arrangement of structural units. Whether a compound is crystalline and the respective crystal system can, for example, be confirmed by means of X-ray diffraction. Preferably, the crystalline zwitterionic zinc(II)-carboxylate compound comprises and in particular essentially consists of crystals possessing a crystal system selected from monoclinic or triclinic, in particular triclinic.

The method of the present invention comprises steps of:
(i) preparing a mixture comprising zinc(II) ions and a first pyridyl ligand which first pyridyl ligand is a zwitterionic pyridyl ligand having three carboxylic acid moieties; the mixture preferably further comprises $NO3^-$ ions;
(ii) subjecting the mixture to conditions under which a precipitate is formed and separating the precipitate;
(iii) adding a solvent and optionally a second pyridyl ligand to the separated precipitate and subjecting the obtained mixture to conditions under which crystals of the zwitterionic zinc(II)-carboxylate compound are formed;
(iv) separating the crystals of the zwitterionic zinc(II)-carboxylate compound.

The term "pyridyl ligand" as used herein generally refers to ligands comprising at least one optionally substituted pyridine ring.

The first pyridyl ligand is a pyridyl ligand which has three carboxylic acid moieties, which means herein three free carboxylic acid functions. Those three carboxylic acid moieties are preferably directly or indirectly attached to the at least one pyridine ring. The first pyridyl ligand is zwitterionic, i.e. is a molecule with both positive and negative electrical charges.

The first pyridyl ligand preferably has a structure of Formula (I):

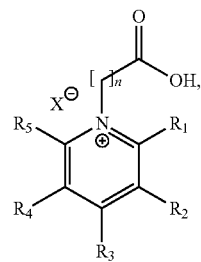

Formula (I)

wherein X is a halogen. X is more preferably selected from Br, Cl or I and most preferably Br. n is an integer and selected from 0, 1, 2 or 3, more preferably 1 or 2 and in particular 1. Two of $R^1$ to $R^5$ are a group of Formula (II) and the other of $R^1$ to $R^5$ being hydrogen:

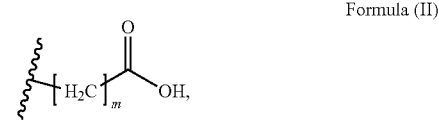

Formula (II)

with m being an integer and selected from 0, 1 or 2. m is more preferably selected from 0 or 1 and in particular m is 0, i.e. the carboxyl groups are directly attached to carbon atoms in the pyridine ring. Preferably, $R^2$ and $R^4$ are a group of Formula (II) each and $R^1$, $R^3$ and $R^5$ are hydrogen.

The first pyridyl ligand has more preferably a structure of Formula (III):

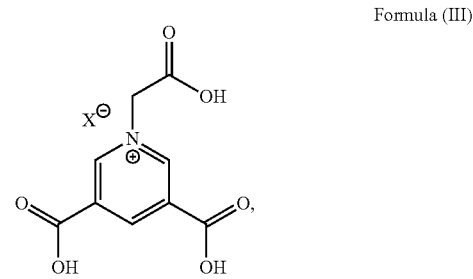

Formula (III)

with X being as defined above, preferably Br, Cl or I and most preferably Br.

The feature that the mixture comprises the pyridyl ligand as used herein is to be understood to cover any protonated or deprotonated form of said pyridyl ligand due to the presence of further components in the mixture added, for example, for dissolving it.

Step (i) preferably comprises steps of:
a) preparing a first pre-mixture comprising mixing the first pyridyl ligand and a solvent;
b) preparing a second pre-mixture comprising mixing a zinc(II) salt and a solvent;
c) adding the pre-mixture of step b) to the pre-mixture of step a).

The first pyridyl ligand in step a) is preferably of Formula (III) with X being Br. The solvent in step a) is preferably an aliphatic alcohol, which means herein an aliphatic hydrocarbon, preferably a branched or straight chain alkane, wherein at least one hydrogen atom of the aliphatic hydrocarbon is substituted with a hydroxyl group, preferably one hydrogen atom is substituted with a hydroxyl group referenced as monohydric aliphatic alcohol. More preferably, the aliphatic alcohol is a monohydric aliphatic alcohol, still more preferably a monohydric alcohol with 1 to 3 carbon atoms, further preferably with 1 to 2 carbon atoms. I.e. the aliphatic alcohol is more preferably selected from methanol, ethanol, propanol or isopropanol or mixtures thereof and further preferably from methanol, ethanol or mixtures thereof. More preferably, the aliphatic alcohol is methanol. The solvent in step a) most preferably essentially consists of methanol.

Step a) preferably further comprises a step of adjusting the pH to a pH of between 6.5 and 7.5, more preferably to a pH of about 7.0. The pH is preferably adjusted by adding a base. The base is preferably an alkali hydroxide. Alkali hydroxides are a class of chemical compounds which are composed of an alkali metal cation, i.e. one of lithium (Li), sodium (Na), potassium (K), rubidium (Rb), caesium (Cs), and the hydroxide anion (HO—). In particular, the alkali metal cation is K or Na. More preferably, the base is NaOH, i.e. sodium hydroxide. In such embodiments, the first pre-mixture comprises the solvent of step a) and NaOH.

The zinc(II) salt of step b) is preferably a hydrate of $Zn(NO_3)_2$, in particular the hexahydrate. Thus, the zinc(II) salt is most preferably $Zn(NO_3)_2 \times 6\ H_2O$.

The solvent in step b) preferably comprises an aliphatic alcohol, preferably a monohydric aliphatic alcohol. More preferably, the aliphatic alcohol is a monohydric alcohol with 1 to 3 carbon atoms, further preferably with 1 to 2 carbon atoms. I.e. the aliphatic alcohol is more preferably selected from methanol, ethanol, propanol or isopropanol or mixtures thereof and further preferably from methanol, ethanol or mixtures thereof. More preferably, the aliphatic alcohol is methanol. The solvent in step b) most preferably essentially consists of methanol. In especially preferred embodiments, both solvents in step a) and step b) essentially consist of methanol.

The mixture prepared in step (i) is preferably a solution, i.e. a homogeneous mixture comprising the zinc(II) ions and the first pyridyl ligand in the solvents from step a) and b) and optionally the base, in particular both solvents essentially consist of methanol and the base is NaOH. In particular, the first pre-mixture prepared in step a) is a solution comprising the first pyridyl ligand in methanol and NaOH and the second pre-mixture prepared in step b) is a solution comprising the zinc(II) salt, in particular $Zn(NO_3)_2 \times 6\ H_2O$, in methanol.

The mixture in step (i) is most preferably prepared by suspending the first pyridyl ligand of Formula (III) with X being Br in methanol and adjusting the pH to about 7.0 by means of NaOH, preparing a solution of $Zn(NO_3)_2 \times 6\ H_2O$ in methanol and adding said solution to the solution comprising the first pyridyl ligand. The first pyridyl ligand and the $Zn(NO_3)_2 \times 6\ H_2O$ are preferably used for preparing the mixture, in particular solution, in equimolar amounts.

The term precipitate as known in the art generally refers to the solid formed from a mixture such as formed from a liquid solution, wherein the process of the formation of the solid is generally called "precipitation". Thus, "precipitate" as used herein means the solid formed from the mixture of step (i), preferably from the solution prepared in step (i). The conditions under which a precipitate is formed in step (ii) preferably include and most preferably the precipitate is formed by stirring the mixture after step (i) for between 15 min and 60 min, more preferably for about 30 min, for forming the precipitate. Stirring is in particular carried out at a temperature of between 20° C. and 30° C., more preferably at about 25±2° C. The precipitate is preferably separated by filtration.

Step (ii) can further comprise a step of purifying the precipitate. Preferably, the precipitate is purified by washing with a washing solvent. The washing solvent preferably comprises an aliphatic alcohol, in particular a monohydric alcohol with 1 to 3 carbon atoms, further preferably with 1 to 2 carbon atoms. I.e. the aliphatic alcohol is more preferably selected from methanol, ethanol, propanol or isopropanol or mixtures thereof and further preferably from methanol, ethanol or mixtures thereof. More preferably, the aliphatic alcohol is methanol. The washing solvent most preferably essentially consists of methanol.

The method of the present invention further comprises a step (iii) of adding a solvent and optionally a second pyridyl ligand to the separated precipitate and subjecting the obtained mixture to conditions under which crystals of the zwitterionic zinc(II)-carboxylate compound are formed, i.e. under which crystallization occurs. Said step (iii) preferably comprises steps of:
  a) adding the solvent, which solvent comprises and in particular essentially consists of water at a temperature of between 20° C. and 30° C.;
  b) filtering the mixture for obtaining a filtrate and a residue;
  c) optionally adding the second pyridyl ligand to the filtrate;
  d) subjecting the filtrate after step b) or c) to a temperature between 20° C. and 30° C. for at least 48 hours for forming crystals of the zwitterionic zinc(II)-carboxylate compound, in particular the filtrate is allowed to stand at a temperature between 20° C. and 30° C. for at least 48 hours.

The temperatures in step a) and d) are preferably about 25±2° C. Preferably, the filtrate after step b) or c) is allowed to stand at a temperature between 20° C. and 30° C., in particular at about 25±2° C. for more than 48 hours up to 2 weeks. In preferred embodiments, the second pyridyl ligand is added to the filtrate in step c) and the filtrate after step c), i.e. which comprises the second pyridyl ligand, is subjected to a temperature between 20° C. and 30° C. for at least 48 hours. The second pyridyl ligand may be added in form of a mixture such as a solution in a solvent, in particular the second pyridyl ligand is added in form of a mixture in a solvent comprising and in particular essentially consisting of an amide, in particular dimethylformamide (DMF). In such embodiments, the filtrate after step c) comprises a solvent portion comprising and in particular essentially consisting of water and the amide such as DMF.

The method of the present invention further comprises a step (iv) of separating the crystals of the zwitterionic zinc (II)-carboxylate compound. Said step (iv) preferably comprises steps of:
  a) separating the crystals from the mixture;
  b) purifying the crystals;
  c) drying the crystals, preferably by drying the crystals in vacuo.

Preferably, purifying the crystals in step b) comprises and in particular is carried out by means of washing the crystals with a washing solvent. The washing solvent preferably comprises an aliphatic alcohol, in particular a monohydric alcohol, more preferably a monohydric alcohol with 1 to 3 carbon atoms, most preferably methanol. In particular embodiments of the present invention, the washing solvent essentially consists of methanol. In preferred embodiments of the present invention, step (iii) of the method of the present invention comprises adding the second pyridyl ligand, i.e. a second pyridyl ligand is used in step (iii). Said second pyridyl ligand preferably can comprise at least two and in particular two pyridine rings. In preferred embodiments of the present invention, the second pyridyl ligand has a structure selected from Formula (IV), (V) or (VI):

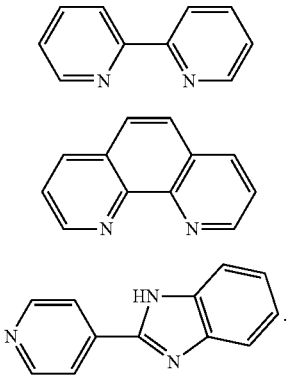

Formula (IV)

Formula (V)

Formula (VI)

The second pyridyl ligand is preferably added in step (iii) in equimolar amounts compared to the first pyridyl ligand. More preferably, the second pyridyl ligand has a structure of Formula (IV).

The present invention in particular encompasses the following preferred embodiments A to D of the method of the present invention:

A. The first pyridyl ligand used in step (i) is of Formula (III):

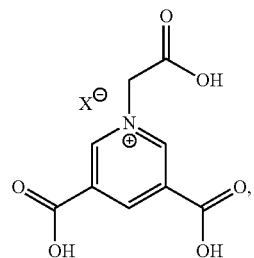

Formula (III)

with X being Br, i.e. zwitterionic N-carboxymethyl-(3,5-dicarboxyl)-pyridinium bromide (H₃CmdcpBr) and no second pyridyl ligand is added in step (iii). In such embodiment, the crystalline zwitterionic zinc(II)-carboxylate compound preferably comprises and in particular essentially consists of at least one 2D coordination polymer, i.e. a coordination polymer with repeating coordination entities extending in two dimensions, comprising and in particular essentially consisting of repeating coordination entities with the formula [Zn(Cmdcp)(H₂O)], i.e. which crystalline zwitterionic zinc(II)-carboxylate compound can in embodiments be described as [Zn(Cmdcp)(H₂O)]$_n$ (also referenced as compound 1). In compound 1, a zinc(II) central atom is coordinated by one water molecule forming [Zn(H₂O)] subunits, wherein each first pyridyl ligand bridges three [Zn(H₂O)] subunits through the carboxylic acid moieties. The zinc(II) central atoms adopt a tetrahedral coordination geometry. The crystal system is monoclinic.

B. The first pyridyl ligand in step (i) is of Formula (III):

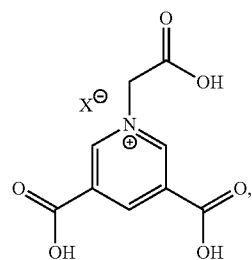

Formula (III)

with X being Br and the second pyridyl ligand added in step (iii) is of Formula (IV):

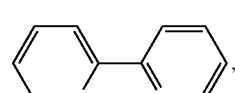

Formula (IV)

i.e. 2,2'-bipyridine (bipy).

In such embodiment, the crystalline zwitterionic zinc(II)-carboxylate compound comprises and in particular essentially consists of at least one 1D coordination polymer, i.e. a coordination polymer with repeating coordination entities extending in one dimension, comprising and in particular essentially consisting of repeating coordination entities with the formula {[Zn₂(Cmdcp)(bipy)₂(H₂O)₅](NO₃)₂.3H₂O}, i.e. which crystalline zwitterionic zinc(II)-carboxylate compound can in embodiments be described as {[Zn₂(Cmdcp)(bipy)₂(H₂O)₅](NO₃)₂.3H₂O}$_n$ (also referenced as compound 2). In compound 2, a zinc(II) central atom is coordinated by two water molecules and one bipy molecule forming [Zn(bipy)(H₂O)₂]²⁺ subunits and with three water molecules and one bipy molecule forming [Zn(bipy)(H₂O)₃]²⁺ subunits, wherein each first pyridyl ligand bridges two [Zn(bipy)(H₂O)₂]²⁺ subunits and one [Zn(bipy)(H₂O)₃]²⁺ subunit through the carboxylic acid moieties. The zinc(II) central atoms adopt an octahedral coordination geometry. The crystal system is triclinic. NO₃⁻ anions are present in compound 2 to balance the positive charge of the pyridium cations and/or zinc(II) centers.

C. The first pyridyl ligand in step (i) is of Formula (III):

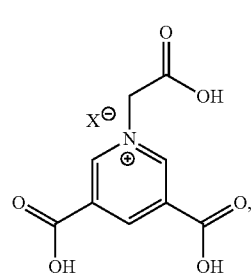

Formula (III)

with X being Br and the second pyridyl ligand added in step (iii) is of Formula (V):

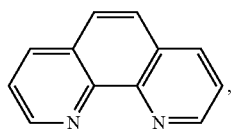

i.e. 1,10-phenanthroline (phen).

In such embodiment, the crystalline zwitterionic zinc(II)-carboxylate compound comprises and in particular essentially consists of [Zn(phen)(H$_2$O)$_4$]$^{2+}$ dications and [Cmdcp]$^{2-}$ dianions, i.e. [Zn(phen)(H$_2$O)$_4$] [Cmdcp] (also referenced as compound 3). The zinc(II) central atoms adopt an octahedral coordination geometry in compound 3 which is completed by two nitrogen atoms of phen and four H$_2$O molecules. The crystal system is triclinic.

D. The first pyridyl ligand in step (i) is of Formula (III):

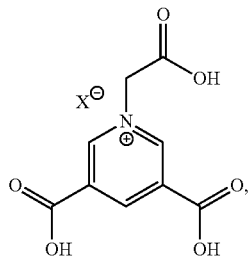

Formula (III)

with X being Br and the second pyridyl ligand added in step (iii) is of Formula (VI):

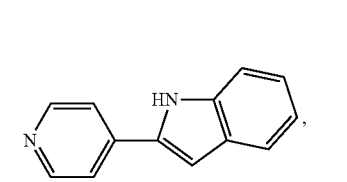

Formula (VI)

i.e. 2-(pyridin-4-yl)-1H-benzo[d]imidazole (pbz).

In such embodiment, the crystalline zwitterionic zinc(II)-carboxylate compound preferably comprises and in particular essentially consists of at least one 2D coordination polymer, i.e.

a coordination polymer with repeating coordination entities extending in two dimensions, comprising and in particular essentially consisting of repeating coordination entities with the formula {[Zn(Cmdcp)(pbz)][pbz].7H$_2$O}, i.e. which crystalline zwitterionic zinc(II)-carboxylate compound can in embodiments be described as {[Zn(Cmdcp)(pbz)][pbz].7H$_2$O}$_n$ (also referenced as compound 4). In compound 4, each Cmdcp ligand bridges three zinc(II) central atoms through three carbon/late moieties. Thus, each zinc(II) central atom is coordinated to five oxygen atoms from three carboxylic acid moieties of three Cmdcp ligands.

The zinc(II) central atom further coordinates to one nitrogen atom from pbz, thereby possessing an octahedral coordination geometry. The crystal system is monoclinic.

Most preferably, the first pyridyl ligand has a structure of Formula (III) with X being Br and wherein in step (iii) the second pyridyl ligand is added and said second pyridyl ligand has a structure of formula (IV) for forming a crystalline zwitterionic zinc(II)-carboxylate compound according to the above embodiment B which can be described by the formula {[Zn$_2$(Cmdcp)(bipy)$_2$(H$_2$O)$_5$](NO$_3$)$_2$.3H$_2$O}$_n$, i.e. which is in particular compound 2.

The present invention further provides a crystalline zwitterionic zinc(II)-carboxylate compound obtained or obtainable by the method described above. In one embodiment of the present invention, the present invention provides a crystalline zwitterionic zinc(II)-carboxylate compound obtained by the method described above. In another embodiment of the present invention, the present invention provides a crystalline zwitterionic zinc(II)-carboxylate compound obtainable by the method described above.

The zinc(II) central atom preferably possesses a tetrahedral or octahedral coordination geometry, more preferably an octahedral coordination geometry. The crystalline zwitterionic zinc(II)-carboxylate compound preferably comprises and more preferably essentially consists of crystals with a monoclinic or triclinic crystal system, more preferred a triclinic crystal system.

The crystalline zwitterionic zinc(II)-carboxylate compound in preferred embodiments of the present invention comprises a coordination polymer extending through repeating coordination entities in one or two dimensions, i.e. more preferably comprises and in particular essentially consists of at least one 1D or 2D coordination polymer, most preferably at least one 1D coordination polymer.

The crystalline zwitterionic zinc(II)-carboxylate compound is in most preferred embodiments obtained or obtainable by the method described above in which the first pyridyl ligand in step (i) has a structure of Formula (III)

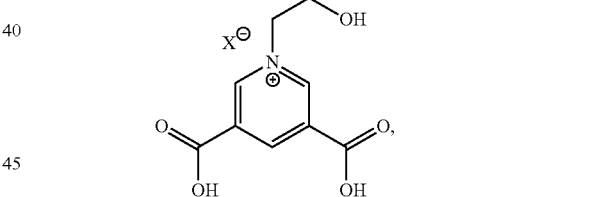

Formula (III)

with X being Br and wherein the second pyridyl ligand added in step (iii) has a structure of Formula (IV):

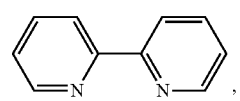

Formula (IV)

which crystalline zwitterionic zinc(II)-carboxylate compound is according to embodiment B described above and can be described by the formula {[Zn$_2$(Cmdcp)(bipy)$_2$(H$_2$O)$_5$](NO$_3$)$_2$.3H$_2$O}$_n$, i.e. is compound 2.

The present invention in a third aspect provides a method of detecting a target nucleic acid sequence in a sample. The sample is from a subject such as a mammal, preferably a human and can comprise, for example, blood or serum.

The method of the present invention of detecting a target nucleic acid sequence in a sample comprises steps of:

(i) preparing a mixture of a crystalline zwitterionic zinc (II)-carboxylate compound obtained or obtainable with the preparation method described above and an oligonucleotide probe having a nucleic acid sequence at least partially complementary to said target nucleic acid sequence and being labeled with a fluorescent;
(ii) incubating the mixture with the sample;
(iii) measuring the fluorescence after step (ii);
(iv) determining the presence and/or amount of the target nucleic acid sequence in the sample based on the fluorescence.

The crystalline zwitterionic zinc(II)-carboxylate compound used in step (i) of the method of detecting a target nucleic acid sequence preferably comprises and in particular essentially consists of at least one coordination polymer with repeating coordination entities extending in one dimension, i.e. a 1D coordination polymer in particular a 1D sheet network. Such compounds proved to allow for an exceptional interaction with the oligonucleotide probe and quenching efficiency. The crystalline zwitterionic zinc(II)-carboxylate compound used in step (i) is most preferably obtained or obtainable by the method described above in which the first pyridyl ligand in step (i) has a structure of Formula (III):

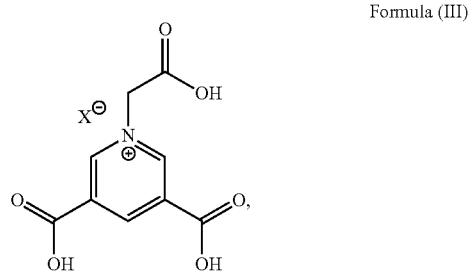

Formula (III)

with X being Br and wherein the second pyridyl ligand added in step (iii) has a structure of Formula (IV):

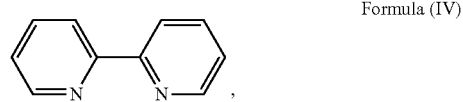 [SMILES: c1ccc(-c2ccccn2)nc1]

Formula (IV)

which crystalline zwitterionic zinc(II)-carboxylate compound is according to embodiment B described above and can be described by the formula $\{[Zn_2(Cmdcp)(bipy)_2(H_2O)_5](NO_3)_2 \cdot 3H_2O\}_n$, i.e. is preferably compound 2. The inventors found that such crystalline zwitterionic zinc(II)-carboxylate compound is especially advantageous and provides an exceptional quenching efficiency at a low saturation concentration and a particularly high specificity when using an oligonucleotide probe of SEQ. ID. NO:1 and a HIV-1 ds-DNA target nucleic acid sequence of SEQ. ID. NO:2 and NO:3.

The target nucleic acid sequence is of DNA or RNA, in particular viral DNA or RNA such as from HIV such as HIV-1, Ebola virus or Dengue virus, more preferably from HIV-1 such as HIV-1 ds-DNA comprising or consisting of SEQ. ID. NO:2 and SEQ. ID. NO:3 which includes a sequence corresponding to the polypurine tract sequence (PPT) of HIV-1 RNA which plays an important role in the viral life-cycle.

The term "oligonucleotide probe" as known in the art refers to a short single-stranded sequence of nucleotides that are synthesized to match a specific region of DNA or RNA used as a molecular probe to detect said sequence. Said oligonucleotide probe is labeled with a fluorescent, more preferably FAM (fluorescein) is attached to the oligonucleotide probe. The oligonucleotide probe is preferably made up of 10 to 25 nucleotides and more preferably comprises or consists of SEQ. ID. NO: 1, most preferably it is a FAM-labeled ss-DNA sequence comprising or consisting of SEQ. ID. NO:1.

The incubation in step (ii) of the method of detecting a target nucleic acid sequence is preferably carried out for at least 45 min, more preferably for about 60 min.

The wavelength for determining the fluorescence in step (iii) of the method of detecting a target nucleic acid sequence depends on the fluorescent. The skilled person is able to determine the respective absorption and emission wavelength.

Step (iv) of the method of detecting a target nucleic acid sequence may further comprise a step of comparing the fluorescence with at least one reference value such as the fluorescence of a reference sample without the target nucleic acid sequence or at least one reference sample with a predetermined amount of target nucleic acid sequence.

The inventors found that in step (i) the zwitterionic zinc(II)-carboxylate compound can non-covalently bind to the oligonucleotide probe and thereby quench the fluorescence of said oligonucleotide probe. The oligonucleotide probe in step (ii) can then bind to the target nucleic acid sequence in the sample leading to a fluorescence regeneration as the oligonucleotide probe will be released from the zwitterionic zinc(II)-carboxylate compound depending on the concentration of the target nucleic acid sequence as the configuration between the oligonucleotide probe and the zwitterionic zinc(II)-carboxylate compound will be affected.

Hence, the method and the crystalline zwitterionic zinc(II)-carboxylate compound can be used in the diagnosis of HIV infections as well as other virus associated infectious diseases, such as Ebola, Dengue and the like.

Still further, a kit is provided with the present invention comprising:
(i) a zwitterionic zinc(II)-carboxylate compound obtained or obtainable with the preparation method described above;
(ii) an oligonucleotide probe having a nucleic acid sequence complementary to a target nucleic acid sequence and being labeled with a fluorescent, in particular a FAM-labeled oligonucleotide probe of SEQ. ID. NO:1.

The crystalline zwitterionic zinc(II)-carboxylate compound in the kit is preferably obtained or obtainable by the preparation method described above in which the first pyridyl ligand in step (i) of the preparation method has a structure of Formula (III)

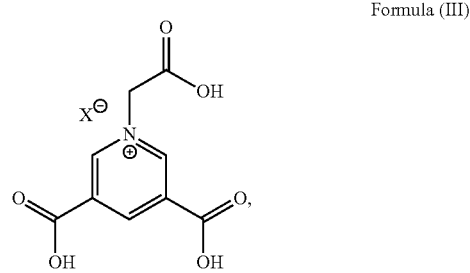

Formula (III)

with X being Br and wherein the second pyridyl ligand added in step (iii) of the preparation method has a structure of Formula (IV):

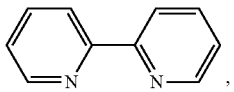

Formula (IV)

which crystalline zwitterionic zinc(II)-carboxylate compound is according to embodiment B described above and can be described by the formula $\{[Zn_2(Cmdcp)(bipy)_2(H_2O)_5](NO_3)_2 \cdot 3H_2O\}_n$, i.e. is preferably compound 2.

In a further aspect, the present invention refers to the use of the crystalline zwitterionic zinc(II)-carboxylate compound obtained or obtainable by the preparation method as described above or the kit in the diagnosis of viral infectious diseases, preferably of HIV-1. More specifically, the present invention refers to the use of the crystalline zwitterionic zinc(II)-carboxylate compound or the kit for detecting the presence and/or the amount of a target nucleic acid, in particular HIV-1 ds-DNA preferably of SEQ. ID. NO: 2 and 3, in a sample from a subject such as a human.

EXAMPLES

IR spectra were recorded on a Nicolet MagNa-IR 550 infrared spectrometer. Elemental analyses for C, H and N were performed on an EA1112 CHNS elemental analyzer. The fluorescence spectra and fluorescence anisotropy were measured on LS55 fluorescence spectrophotometer. Zeta potential measurement was carried out on NanoZS90 zeta-sizer. Powder X-ray diffraction (PXRD) spectra were recorded on a Rigaku D/max-2200/PC. The X-ray generated from a sealed Cu tube was mono-chromated by a graphite crystal and collimated by a 0.5 mm MONOCAP ($\lambda$Cu-K$\alpha$=1.54178 Å). The tube voltage and current were 40 kV and 40 mA, respectively. Samples for PXRD were prepared by placing thin layers of samples on zero-background silicon (510) crystal plates.

All the DNA sequences were purchased from Sangon Inc. (Shanghai, China) and are shown in table 1 below.

The synthesis of $H_3$CmdcpBr and the method for the detection of HIV-1 ds-DNA were as reported in Chen, J. X. et al. and Yang, S. P. et al., respectively (Bent Tritopic Carboxylates for Coordination Networks: Clues to the Origin of Self-penetration, CrystEngComm. 2014, 16, 7722-7730, Platforms formed from a 3D Cu-based zwitterionic metal-organic framework and probe ss-DNA: selective fluorescent biosensors for HIV-1 ds-DNA and Sudan virus RNA sequences, Anal. Chem. 2015, 87, 12206-12214). Duplex DNA was prepared according to Chen, L. et al. (Metal-organic frameworks-based biosensor for sequence-specific recognition of double-stranded DNA. Analyst. 2013; 138 (12): 3490-3). All DNA samples were dissolved in 100 nM Tris-HCl buffer solution (pH 7.4, 100 mM NaCl, 5 mM $MgCl_2$) and stored at 4° C. for use. All the other reagents and solvents were obtained from commercial sources and used without further purification.

Example 1

Synthesis of crystalline zwitterionic zinc(II)-carboxylate compounds of the present invention $H_3$CmdcpBr (61.2 mg, 0.2 mmol) as first pyridyl ligand was suspended in methanol as solvent (5 mL), and the pH was adjusted to 7.0 with 0.1 M sodium hydroxide solution to give a clear solution. A solution of $Zn(NO_3)_2 \cdot 6H_2O$ (60.2 mg, 0.2 mmol) in methanol as solvent (5 mL) was then added. After stirring for 30 min, the formed white precipitate was collected by filtration, washed with methanol (5 mL), and re-dissolved in $H_2O$ (30 mL) at room temperature and filtered to afford a clear colorless solution.

Further Synthesis of $[Zn(Cmdcp)(H_2O)]_n$ (Compound 1)

The above-mentioned solution was allowed to stand at room temperature for two weeks to give colorless crystals. The resulting crystals were collected, washed with methanol and dried in vacuo to give compound 1 (55 mg, 89%). Anal. Calcd. for $C_9H_7ZnNO_7$: C 35.26, H 2.30, N 4.57. Found: C 35.75, H 2.35, N 4.86. IR (KBr disc, cm$^{-1}$) v 3477 (s), 3085 (s), 1655 (s), 1617 (s), 1240 (m), 1175 (m), 988 (w), 930 (w), 733 (m), 690 (m), 620 (m), 561 (m), 461 (w).

TABLE 1

DNA sequences used in the present invention

| | comprises SEQ. ID. NO. | Sequence |
|---|---|---|
| Probe DNA | SEQ. ID. NO: 1 | 5'-FAM-TTCTTCTTTTTTCT-3' |
| Complementary target HIV-1 ds-DNA ($T_0$) | SEQ. ID. NO: 2 and NO: 3 | 5'-$^1$C$^2$G$^3$A$^4$G5T$^6$T$^7$A$^8$A$^9$G$^{10}$A$^{11}$A$^{12}$G$^{13}$A$^{14}$A$^{15}$A$^{16}$A$^{17}$A$^{18}$A$^{19}$G$^{20}$A$^{21}$T$^{22}$T$^{23}$G$^{24}$A$^{25}$G$^{26}$C-3'/5'-$^{27}$G$^{28}$C$^{29}$T$^{30}$C$^{31}$A$^{32}$A$^{33}$T$^{34}$C$^{35}$T$^{36}$T$^{37}$T$^{38}$T$^{39}$T$^{40}$T$^{41}$C$^{42}$T$^{43}$T$^{44}$C$^{45}$T$^{46}$T$^{47}$A$^{48}$A$^{49}$C$^{50}$T$^{51}$C$^{52}$G-3' |
| One base pair mutated for complementary target HIV ds-DNA ($T_1$) | SEQ. ID. NO: 4 and NO: 5 | 5'-$^1$C$^2$G$^3$A$^4$G5T$^6$T$^7$A$^8$A$^9$G$^{10}$A$^{11}$A$^{12}$A$^{13}$A$^{14}$A$^{15}$A$^{16}$A$^{17}$A$^{18}$A$^{19}$G$^{20}$A$^{21}$T$^{22}$T$^{23}$G$^{24}$A$^{25}$G$^{26}$C-3'/5'-$^{27}$G$^{28}$C$^{29}$T$^{30}$C$^{31}$A$^{32}$A$^{33}$T$^{34}$C$^{35}$T$^{36}$T$^{37}$T$^{38}$T$^{39}$T$^{40}$T$^{41}$T$^{42}$T$^{43}$T$^{44}$C$^{45}$T$^{46}$T$^{47}$A$^{48}$A$^{49}$C$^{50}$T$^{51}$C$^{52}$G-3' |
| Complementary ss-DNA ($T_2$) | SEQ. ID. NO: 6 | 5'-$^1$A$^2$G$^3$A$^4$A$^5$A$^6$A$^7$A$^8$A$^9$G$^{10}$A$^{11}$A$^{12}$G$^{13}$A$^{14}$A-3' |
| One base pair mutated for complementary ss-DNA ($T_3$) | SEQ. ID. NO: 7 | 5'-$^1$A$^2$G$^3$A$^4$A$^5$C$^6$A$^7$A$^8$A$^9$G$^{10}$A$^{11}$A$^{12}$G$^{13}$A$^{14}$A-3' |
| Non-specific ss-DNA ($T_4$) | SEQ. ID. NO: 8 | 5'-GCTAGAGATTTTCCACACTGACT-3' |

Further Synthesis of {[Zn$_2$(Cmdcp)(bipy)$_2$(H$_2$O)$_5$](NO$_3$)$_2$·3H$_2$O}$_n$ (Compound 2)

The above-mentioned solution was treated with the second pyridyl ligand bipy (31.2 mg, 0.2 mmol) in 5 mL DMF to give a clear colorless solution. The solution was allowed to stand at ambient temperature for several days to give colorless crystals. The resulting crystals were collected, washed with methanol and dried in vacuo to give compound 2 (70 mg, 75%). Anal. Calcd. For C$_{29}$H$_{37}$N$_7$O$_{20}$Zn$_2$: C 37.28, H 3.99, N 10.49. Found: C 37.18, H 3.76, N 9.98. IR (KBr disc, cm$^{-1}$) v 3361 (s), 2359 (m), 1646 (s), 1604 (s), 1382 (s), 1180 (w), 1022 (w), 908 (w), 819 (w), 768 (m), 732 (m), 629 (w).

Further Synthesis of {[Zn(phen)(H$_2$O)$_4$][Cmdcp]} (Compound 3)

Compound 3 was prepared using the same method as described for the preparation of compound 2, but using phen (35.6 mg, 0.2 mmol) as second pyridyl ligand. Yield: 91 mg, 84%. Anal. Calcd. for C$_{21}$H$_{21}$ZnN$_3$O$_{10}$: C 46.64, H 3.91, N 7.77. Found: C 46.99, H 3.87, N 7.82. IR (KBr disc, cm$^{-1}$) v 3391 (s), 3176 (s), 1667 (s), 1622 (s), 1439 (s), 1361 (s), 1281 (w), 1230 (m), 1178 (w), 1108 (w), 1031 (w), 968 (w), 920 (s), 839 (m), 742 (m), 687 (w), 628 (m).

Further Synthesis of {[Zn(Cmdcp)(pbz)][pbz]·7H$_2$O}$_n$ (Compound 4)

Compound 4 as light yellow crystals was prepared using the same method as described for the preparation of compound 2, but using pbz (39.4 mg, 0.2 mmol) as an second pyridyl ligand. Yield: 58 mg, 73%. Anal. Calcd. for C$_{33}$H$_{31}$ZnN$_7$O$_{13}$: C 49.61, H 3.91, N 12.27. Found: C 49.99, H 3.87, N 12.32. IR (KBr disc, cm$^{-1}$) v 3391 (s), 3176 (s), 1667 (s), 1622 (s), 1439 (m), 1361 (s), 1281 (w), 1230 (m), 1178 (w), 1108 (w), 968 (w), 921 (w), 839 (m), 742 (s), 687 (w), 628 (w).

Example 2

X-ray crystal structure determinations of the obtained crystalline zwitterionic zinc(II)-carboxylate compounds Crystallographic measurements were made on a Bruker APEX II diffractometer by using graphite-monochromated Mo Kα (λ=0.71073 Å) irradiation. The data were corrected for absorption effects with SADABS (Sheldrick, G. M., SADABS Program for empirical absorption correction of area detector data, University of Gottingen, Germany (1996)). All crystal structures were solved by direct methods and refined on F$^2$ by full-matrix least-squares techniques with SHELXTL-97 program (Sheldrick, G. M., SHELXS-97 and SHELXL-97. Programs for crystal structure solution and refinement. University of Gottingen, Germany (1997)). In compound 1 and compound 3, the hydrogen atom coordinates of water were found from Fourier Map and applied O—H=0.85 Å restraints and U$_{iso}$(H)=1.2U$_{eq}$(O) constraints for the bond lengths and the thermal parameters. The hydrogen atoms on all water molecules in compound 2 and O1W, O2W, O3W and O6W in compound 4 were suggested by Calc-OH program in WinGX suite (Farrugia, L. J., WinGX suite for small molecule single-crystal crystallography. J Appl Cryst. 1999; 32: 837-8). The hydrogen atoms on the O4W, O5W and O7W in compound 4 were not located. Selected bond distances (Å) and angles (°) for compounds 1 to 4 are listed in Tables 2 to 5. A summary of the key crystallographic information is given in Table 6.

TABLE 2

Selected bond distances (Å) and angles (°) for compound 1

| | | | |
|---|---|---|---|
| Zn(1)—O(1) | 1.945(2) | Zn(1)—O(3)#1 | 1.943(2) |
| Zn(1)—O(5)#2 | 1.974(2) | Zn(1)—O(1W) | 1.980(3) |
| O(3)—Zn(1)#3 | 1.943(2) | O(5)—Zn(1)#4 | 1.974(2) |
| O(1)—Zn(1)—O(3)#1 | 97.42(11) | O(1)—Zn(1)—O(5)#2 | 109.70(11) |
| O(3)#1—Zn(1)—O(5)#2 | 122.78(11) | O(1)—Zn(1)—O(1W) | 112.60(12) |
| O(3)#1—Zn(1)—O(1W) | 110.11(10) | O(5)#2—Zn(1)—O(1W) | 104.37(11) |

Symmetry transformations used to generate equivalent atoms:
1 x − 3/2, −y + 3/2, z − 1/2;
2 x − 1/2, −y + 3/2, z + 1/2;
3 x + 3/2, −y + 3/2, z + 1/2;
4 x + 1/2, −y + 3/2, z − 1/2.

TABLE 3

Selected bond distances (Å) and angles (°) for compound 2

| | | | |
|---|---|---|---|
| Zn(1)—O(2W) | 2.096(3) | Zn(1)—O(4)#1 | 2.097(2) |
| Zn(1)—O(5) | 2.116(3) | Zn(1)—N(3) | 2.138(3) |
| Zn(1)—O(1W) | 2.147(3) | Zn(1)—N(2) | 2.155(3) |
| Zn(2)—O(1) | 2.039(3) | Zn(2)—O(4W) | 2.089(3) |
| Zn(2)—O(5W) | 2.124(3) | Zn(2)—N(4) | 2.132(3) |
| Zn(2)—N(5) | 2.140(3) | Zn(2)—O(3W) | 2.168(3) |
| O(2W)—Zn(1)—O(4)#1 | 91.23(11) | O(2W)—Zn(1)—O(5) | 87.55(11) |
| O(4)#1—Zn(1)—O(5) | 96.76(11) | O(2W)—Zn(1)—N(3) | 91.61(13) |
| O(4)#1—Zn(1)—N(3) | 94.78(12) | O(5)—Zn(1)—N(3) | 168.45(12) |
| O(2W)—Zn(1)—O(1W) | 175.28(11) | O(4)#1—Zn(1)—O(1W) | 86.96(11) |
| O(5)—Zn(1)—O(1W) | 88.34(11) | N(3)—Zn(1)—O(1W) | 2.88(12) |
| O(2W)—Zn(1)—N(2) | 93.05(12) | O(4)#1—Zn(1)—N(2) | 170.48(12) |
| O(5)—Zn(1)—N(2) | 91.92(12) | N(3)—Zn(1)—N(2) | 76.61(13) |
| O(1W)—Zn(1)—N(2) | 89.41(12) | O(1)—Zn(2)—O(4W) | 95.48(13) |
| O(1)—Zn(2)—O(5W) | 93.82(11) | O(4W)—Zn(2)—O(5W) | 88.75(12) |
| O(1)—Zn(2)—N(4) | 167.48(13) | O(4W)—Zn(2)—N(4) | 93.66(13) |
| O(5W)—Zn(2)—N(4) | 94.91(12) | O(1)—Zn(2)—N(5) | 93.71(13) |

TABLE 3-continued

Selected bond distances (Å) and angles (°) for compound 2

| | | | |
|---|---|---|---|
| O(4W)—Zn(2)—N(5) | 170.54(13) | O(5W)—Zn(2)—N(5) | 88.39(13) |
| N(4)—Zn(2)—N(5) | 77.60(13) | O(1)—Zn(2)—O(3W) | 84.04(12) |
| O(4W)—Zn(2)—O(3W) | 84.16(14) | O(5W)—Zn(2)—O(3W) | 172.36(13) |
| N(4)—Zn(2)—O(3W) | 88.41(13) | N(5)—Zn(2)—O(3W) | 99.06(14) |

Symmetry transformations used to generate equivalent atoms:
1 x − 1, y, z;
2 x + 1, y, z.

TABLE 4

Selected bond distances (Å) and angles (°) for compound 3

| | | | |
|---|---|---|---|
| Zn(1)—O(2W) | 2.0723(12) | Zn(1)—O(1W) | 2.0773(13) |
| Zn(1)—O(4W) | 2.0962(12) | Zn(1)—O(3W) | 2.1046(14) |
| Zn(1)—N(1) | 2.1530(13) | Zn(1)—N(2) | 2.1560(13) |
| O(2W)—Zn(1)—O(1W) | 94.13(6) | O(2W)—Zn(1)—O(4W) | 97.59(5) |
| O(1W)—Zn(1)—O(4W) | 87.25(5) | O(2W)—Zn(1)—O(3W) | 85.39(5) |
| O(1W)—Zn(1)—O(3W) | 89.17(6) | O(4W)—Zn(1)—O(3W) | 175.49(6) |
| O(2W)—Zn(1)—N(1) | 92.68(5) | O(1W)—Zn(1)—N(1) | 170.67(5) |
| O(4W)—Zn(1)—N(1) | 85.52(5) | O(3W)—Zn(1)—N(1) | 97.75(6) |
| O(2W)—Zn(1)—N(2) | 163.85(6) | O(1W)—Zn(1)—N(2) | 97.47(5) |
| O(4W)—Zn(1)—N(2) | 94.16(5) | O(3W)—Zn(1)—N(2) | 83.59(5) |
| N(1)—Zn(1)—N(2) | 77.20(5) | | |

TABLE 5

Selected bond distances (Å) and angles (°) for compound 4

| | | | |
|---|---|---|---|
| Zn(1)—O(3)#1 | 1.9628(18) | Zn(1)—O(1) | 2.0051(18) |
| Zn(1)—O(5)#2 | 2.0218(18) | Zn(1)—N(1) | 2.023(2) |
| O(3)#1—Zn(1)—O(1) | 108.59(8) | O(3)#1—Zn(1)—O(5)#2 | 104.23(8) |
| O(1)—Zn(1)—O(5)#2 | 95.45(8) | O(3)#1—Zn(1)—N(1) | 133.20(8) |
| O(1)—Zn(1)—N(1) | 104.04(9) | O(5)#2—Zn(1)—N(1) | 105.06(9) |

Symmetry transformations used to generate equivalent atoms:
1 −x − 1/2, y − 1/2, −z + 1/2;
2 −x + 1/2, y − 1/2, −z + 1/2;
3 −x − 1/2, y + 1/2, −z + 1/2;
4 −x + 1/2, y + 1/2, −z + 1/2.

TABLE 6

Crystallographic data for compounds 1 to 4

| Compound | 1 | 2 | 3 | 4 |
|---|---|---|---|---|
| Molecular formula | $C_9H_7ZnNO_7$ | $C_{29}H_{37}Zn_2N_7O_{20}$ | $C_{21}H_{21}ZnN_3O_{10}$ | $C_{33}H_{31}ZnN_7O_{13}$ |
| Formula weight | 306.53 | 934.40 | 540.78 | 799.02 |
| Crystal system | monoclinic | triclinic | triclinic | monoclinic |
| Space group | $P2_1/n$ | P-1 | P-1 | $P2_1/n$ |
| a (Å) | 5.2282(11) | 8.9239(18) | 7.2833(3) | 9.3077(7) |
| b (Å) | 21.367(4) | 14.857(3) | 11.2049(5) | 13.5046(10) |
| c (Å) | 9.4167(19) | 16.346(3) | 13.2406(6) | 28.271(2) |
| α (°) | 90.00 | 116.05(3) | 89.2540(10) | 90.00 |
| β (°) | 104.37(3) | 96.87(3) | 77.3510(10) | 91.9464(9) |
| γ (°) | 90.00 | 94.86(3) | 88.7320(10) | 90.00 |
| V (Å³) | 1019.0(4) | 1910.0(6) | 1054.03(8) | 3551.5(5) |
| Z | 4 | 2 | 2 | 4 |
| T/K | 293(2) | 293(2) | 223(2) | 296(2) |
| $D_{calc}$ (g · cm) | 1.998 | 1.625 | 1.704 | 1.494 |
| μ (cm⁻¹) | 2.440 | 1.347 | 1.233 | 0.768 |
| Total reflections | 9696 | 19994 | 8264 | 39159 |
| Unique reflections | 2090 | 8723 | 4460 | 7803 |
| No. observations | 1819 | 6676 | 4106 | 6926 |
| No. parameters | 163 | 523 | 340 | 487 |
| $R^a$ | 0.0409 | 0.0593 | 0.0248 | 0.0476 |

TABLE 6-continued

Crystallographic data for compounds 1 to 4

| Compound | 1 | 2 | 3 | 4 |
|---|---|---|---|---|
| wR[b] | 0.0924 | 0.1354 | 0.0621 | 0.1340 |
| GOF[c] | 1.099 | 1.042 | 1.050 | 1.061 |
| $\Delta\rho_{max}$ (e Å$^{-3}$) | 0.378 | 1.286 | 0.324 | 1.114 |
| $\Delta\rho_{min}$ (e Å$^{-3}$) | -0.420 | -0.798 | -0.440 | -0.871 |

[a]$R = \Sigma ||F_o| - |F_c||/\Sigma |F_o||$.
[b]$wR = [\Sigma w(F_o^2 - F_c^2)^2/\Sigma w(F_o^2)^2]^{1/2}$.
[c]$GOF = [\Sigma w((F_o^2 - F_c^2)^2)/(n - p)]^{1/2}$, where n = number of reflections and p = total numbers of parameters refined.

Figure 5A:
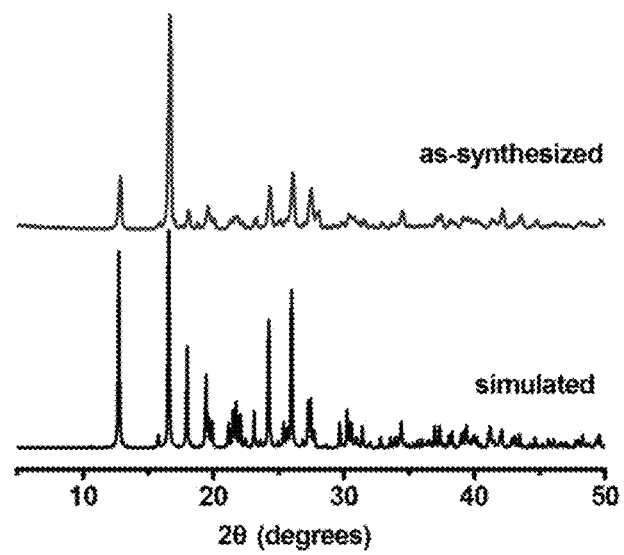
FIGS. 5A, 5B, and 5C show PXRD patterns of compounds 1, 2 and 4 showing agreement between the simulated, as-synthesized after immerse in $H_2O$ for 12 h.
Figure 5B:
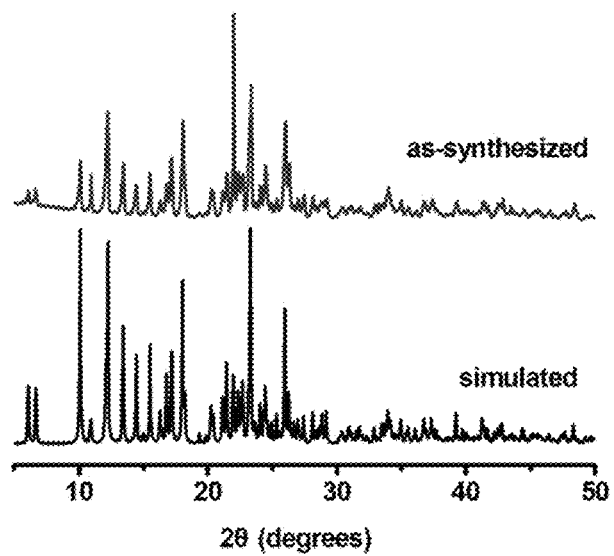
Figure 5C:
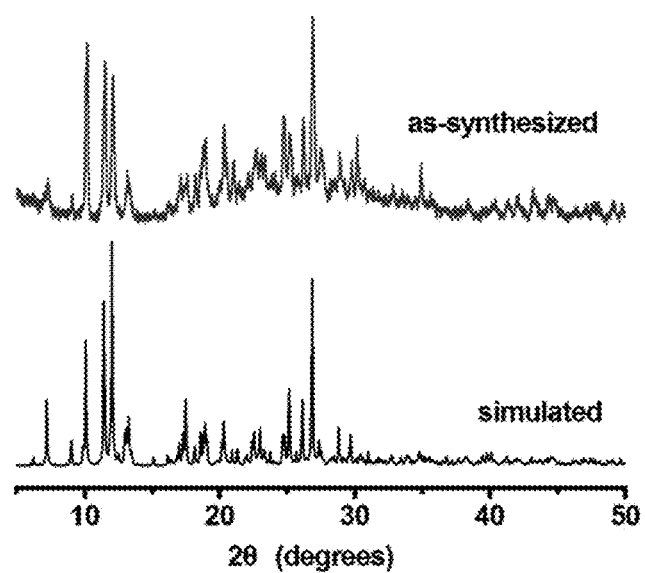

Four water stable compounds were synthesized from the reaction of Zn(NO$_3$)$_2$ with Cmdcp as first pyridyl ligand in water, optionally followed by the addition of bipy, phen or pbz as second pyridyl ligands. Powder X-ray diffraction (PXRD) patterns of a fresh powder of 1, 2 and 4 immersed in H$_2$O for 12 h are in agreement with that of the simulated, indicating their bulky phase purity and water stability (FIG. 5A to 5C).

Crystal Structure of [Zn(Cmdcp)(H$_2$O)]$_n$ (Compound 1)

Compound 1 crystallizes in the monoclinic space group P2$_1$/n and the asymmetric unit consists of one [Zn(Cmdcp)(H$_2$O)] molecule. There is a 2-fold axis located on the central zinc(II) atom that is coordinated by one water molecule, thereby forming a [Zn(H$_2$O)] unit. Each Cmdcp ligand bridges three [Zn(H$_2$O)] units through three terminal carboxylate groups, all in monodentate coordination modes, thereby forming a two-dimensional network as shown in FIG. 1A. The Zn atoms adopt a tetrahedral coordination geometry. Since the methylene groups are used as knots to link one carboxylate and one 3,5-pyridinedicarboxylate, the whole Cmdcp ligand is not linear but exhibits an angular conformation. This makes that all the zinc(II) atoms in the two planes with the distance of 9.61 Å. In compound 1, the average Zn—O (carboxylate) bond length of 1.954(2) Å is comparable to that of Zn—O (water) (1.980 (3) Å), but shorter than that of the mean Zn—O (carboxylate) bond in the reported compound [Zn(1,3,5-HBTC)(1,4-bpeb)]$_n$ (2.041(2) Å; 1,4-bpeb=1,4-bis[2-(4-pyridyl)ethenyl]benzene; 1,3,5-H$_3$BTC=1,3,5-benzenetricarboxylate) (Liu, D. et al., How do substituent groups in the 5-position of 1,3-benzenedicarboxylate affect the construction of supramolecular frameworks? Cryst. Eng. Comm. 2010; 12(11): 3708-16), indicating that the waters and all carboxylate groups interact tightly with the Zn(II) centers.

Crystal Structure of {[Zn$_2$(Cmdcp)(bipy)$_2$(H$_2$O)$_5$](NO$_3$)$_2$·3H$_2$O}$_n$ (Compound 2)

Figure 1B:
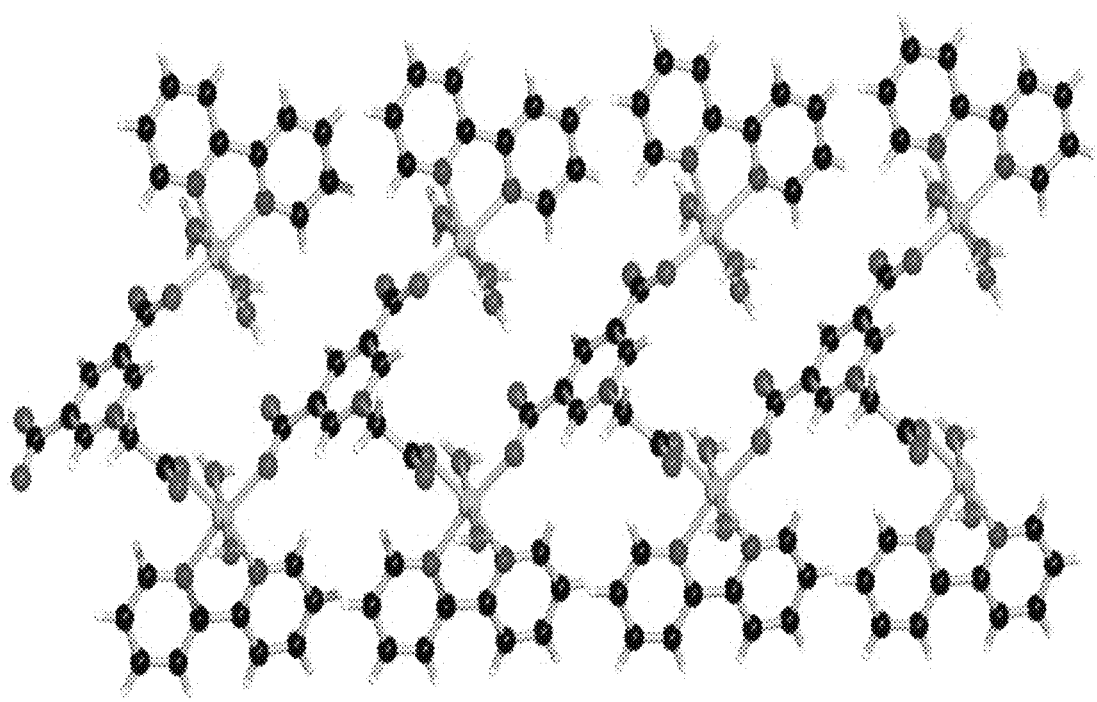
FIG. 1B illustrates the structure of compound 2, namely a 1D coordination polymer with coordination entities $\{[Zn_2(Cmdcp)(bipy)_2(H_2O)_5]NO_3)_2 \cdot 3H_2O\}$ (bipy=2,2'-bipyridine) propagating along the α direction. The $NO_3^-$ anions, all dissociative aqua solvates are omitted.

Compound 2 crystallizes in triclinic space group P-1. The asymmetric unit contains one {[Zn$_2$(Cmdcp)(bipy)$_2$(H$_2$O)$_5$] molecule, two dissociated NO$_3^-$ and three H$_2$O molecules. In compound 2, the Zn(1) atom coordinates to two water molecules and one bipy molecule forming a [Zn(1)(bipy)(H$_2$O)$_2$]$^{2+}$ unit, while Zn(2) atom coordinates to three water molecules and one bipy molecule for the formation of a [Zn(2)(bipy)(H$_2$O)$_3$]$^{2+}$ unit. Each Cmdcp ligand bridges two symmetry-related [Zn(1)(bipy)(H$_2$O)$_2$]$^{2+}$ units and one [Zn(2)(bipy)(H$_2$O)$_3$]$^{2+}$ unit through three carboxylate groups in uniformly monodentate fashion, thus forming a one-dimensional structure along the a axis as show in FIG. 1B. The one-dimensional structures are arranged in parallel with each other and rich in π-π interactions. In compound 2, both zinc(II) atoms adopt octahedral geometries. The NO$_3^-$ anions are present to balance the positive charged of the pyridium cations and/or zinc(II) centers. The Zn—O distances are in the range of 2.096(3)-2.168(3) Å, which is slightly longer than those in compound 1 (from 1.943 (2) to 1.980(3) Å) and [[Zn$_8$(1,3-BDC)$_8$(1,4-bpeb)$_4$]·2H$_2$O] (from 1.9633(17) to 1.9878(14) Å; 1,3-BDC=1,3-benzenedicarboxylic acid) (Liu, D. et al., pH-dependent solvothermal formation of two different 3D multiple interpenetrating nets from the same components of Zn(NO3)2,1,3-benzene-dicarboxylate and 1,4-bis[2-(4-pyridyl)ethenyl]benzene. Cryst. Eng. Comm. 2010; 12: 1912-9). The mean Zn—N bond length of 2.136(3) Å is slightly longer than that in [[Zn$_8$(1,3-BDC)$_8$(1,4-bpeb)$_4$]·2H$_2$O]$_n$ (2.0227(19) Å).

Crystal Structure of [Zn(phen)(H$_2$O)$_4$][Cmdcp] (Compound 3)

Figure 1C:
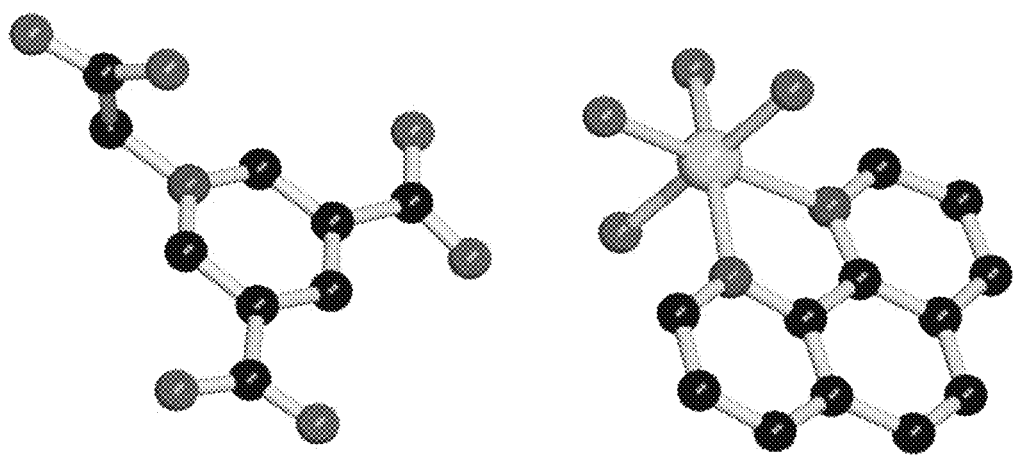
FIG. 1C shows the molecule structure of compound 3, i.e. $[Zn(phen)(H_2O)_4][Cmdcp]$ (phen=1,10-phenanthroline).

Compound 3 crystallizes in the triclinic space group P-1 and each asymmetric unit consists of one {[Zn(phen)(H$_2$O)$_4$]$^{2+}$ dication and one [Cmdcp]$^{2-}$ dianion. In the solid state, the isolated cations co-exist with anions, however, without any obvious interactions between the oxygen donor atoms of carboxylate in [Cmdcp]$^{2-}$ dianions and the metal ions in {[Zn(phen)(H$_2$O)$_4$]$^{2+}$ dications as shown in FIG. 1C. The geometry of the centre Zn$^{2+}$ is octahedron which is completed by two nitrogen atoms of phen and four H$_2$O molecules.

Crystal Structure of [[Zn(Cmdcp)(pbz)][pbz]·7H$_2$O]$_n$ (Compound 4)

Figure 1D:
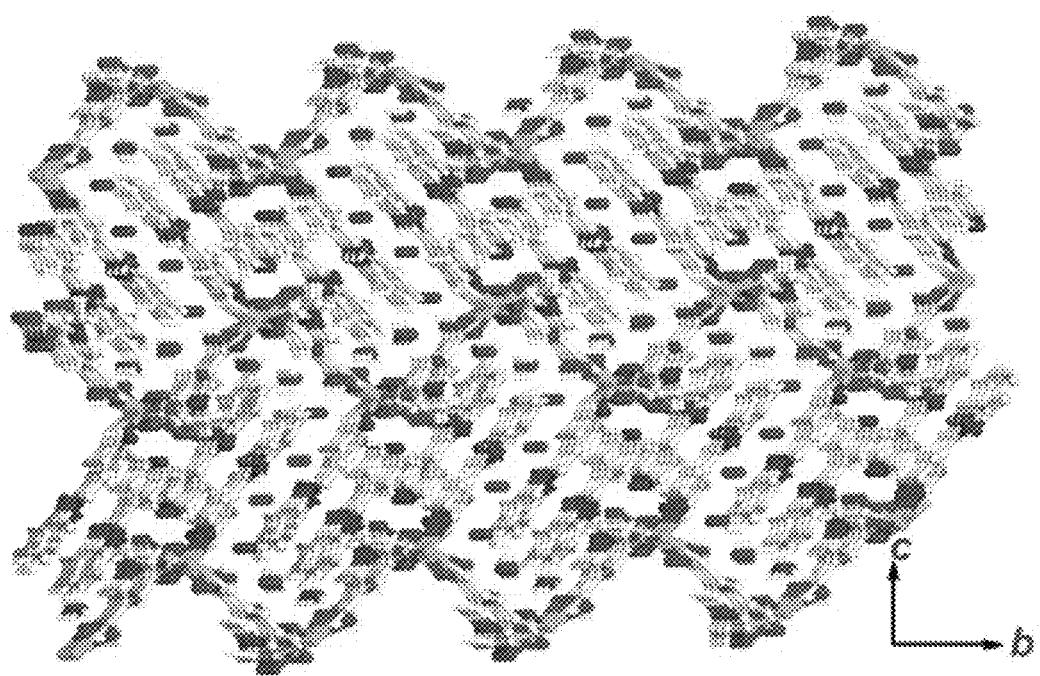
FIG. 1D shows the infinite 2D structure of compound 4 looking down the a axis with coordination entities $\{[Zn(Cmdcp)(pbz)][pbz] \cdot 7H_2O\}$ (pbz=2-(pyridin-4-yl)-1H-benzo[d]imidazole). All hydrogen atoms are omitted. Color codes: Zn (cyan), O (red), N (blue), C (black) for compound 1 to 3 and C (gray) for compound 4.
Figure 1E:
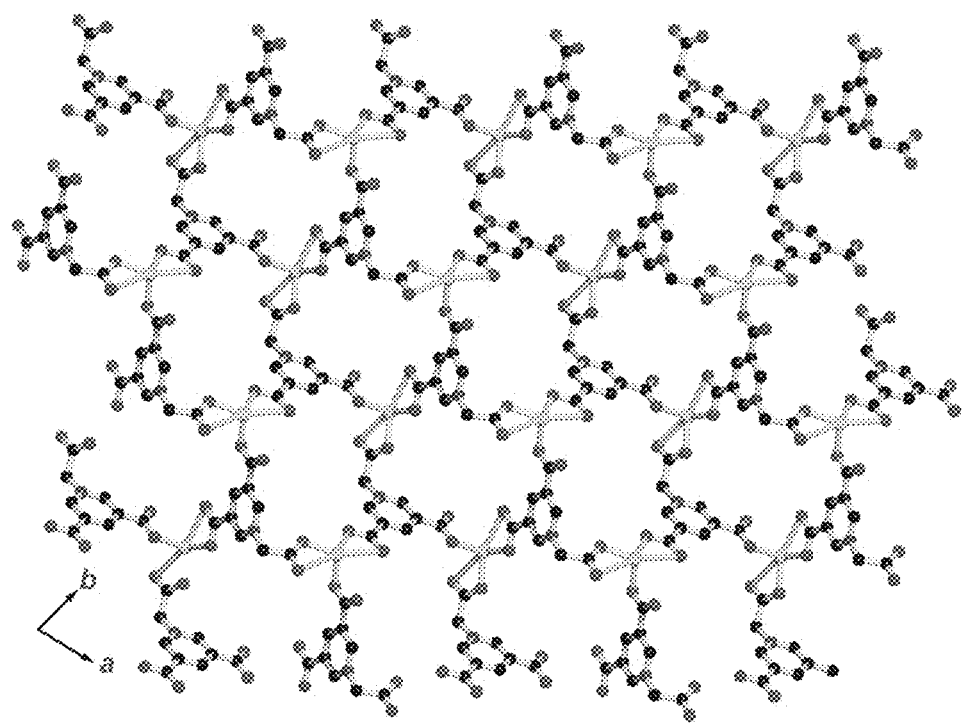
FIG. 1E shows the two-dimensional structure formed by $Zn^{2+}$ and $Cmdcp^{2-}$ ligands in compound 4 looking down the c axis. Color codes: Zn (cyan), O (red), N (blue), C (black).
Figure 1F:
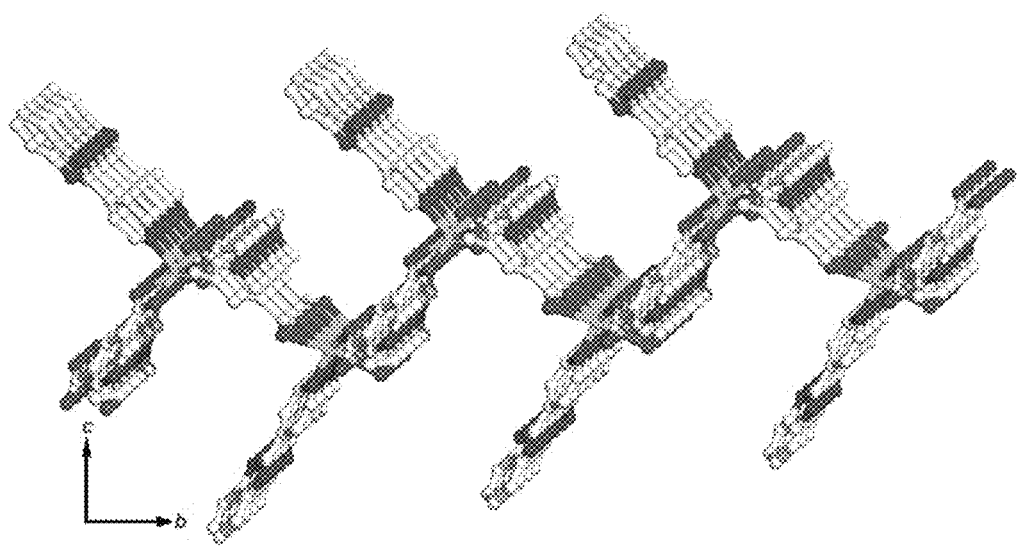
FIG. 1F shows the infinite two-dimensional structure in compound 4 looking down the a axis and all free pbz ligands, water and the hydrogen atoms are omitted for clarity. Color codes: Zn (cyan), O (red), N (blue), C (gray).

Compound 4 crystallizes in the monoclinic space group P2$_1$/n and the asymmetric unit consists of one {[Zn(Cmdcp)(pbz)] molecule, one dissociated pbz molecule and seven free water molecules. Each Cmdcp ligand bridges three Zn$^{2+}$ ions through three carboxylate groups in which one in monodentate coordination mode and the other two in chelating coordination modes, thereby forming a two-dimensional network (FIG. 1E). Each zinc(II) was coordinated to five oxygen atoms from three carboxylates of three Cmdcp ligands, in which two are in chelating coordination modes and the third one in monodentate coordination mode. The zinc(II) further coordinate to one nitrogen atom from pbz, thereby forming octahedral coordination geometry. All the coordinated pbz ligands are decorated on the two sides of the networks (FIG. 1F). All the dissociated pbz and water molecules are packed closely between the networks (FIG. 1D). In compound 4, the mean Zn—O and Zn—N bond lengths (1.997(18) Å vs 2.023(2) Å) are comparable to the corresponding ones found in [Zn(5-Me-1,3-BDC)(1,4-bpeb)]$_n$ (1.937(4) Å vs 2.058(5) Å) (Liu, D. et al., pH-dependent solvothermal formation of two different 3D multiple interpenetrating nets from the same components of Zn(NO3)2,1,3-benzene-dicarboxylate and 1,4-bis[2-(4-pyridyl)ethenyl]benzene. Cryst. Eng. Comm. 2010; 12: 1912-9).

Example 3

Sensing properties of compounds 1 to 4 towards HIV-1 ds-DNA Compounds 1 to 4 contain aromatic rings and positively charged pyridinium and $Zn^{2+}$ cation centers in their structures. The positively charged backbones have been proven to promote electrostatic interactions with the DNA backbone (Wang, G.Y. et al., Two luminescent metal-organic frameworks for the sensing of nitroaromatic explosives and DNA strands. J Mater Chem A. 2014; 2(7): 2213-20, Cui, Y. et al., Luminescent functional metal-organic frameworks. Chem Rev. 2012; 112(2): 1126-62, Morris, W. et al., Nucleic acid-metal organic framework (MOF) nanoparticle conjugates. J Am Chem Soc. 2014; 136(20): 7261-4). Compounds 1 to 4 appear useful to form interactions with fluorophore carboxyfluorescein (FAM)-labeled ss-DNA (probe DNA, P-DNA) through Tr-stacking and electrostatic interactions to quench the fluorescence of FAM, as the latter is composed of aromatic entities laced up by anionic phosphate backbone.

Figure 2A:
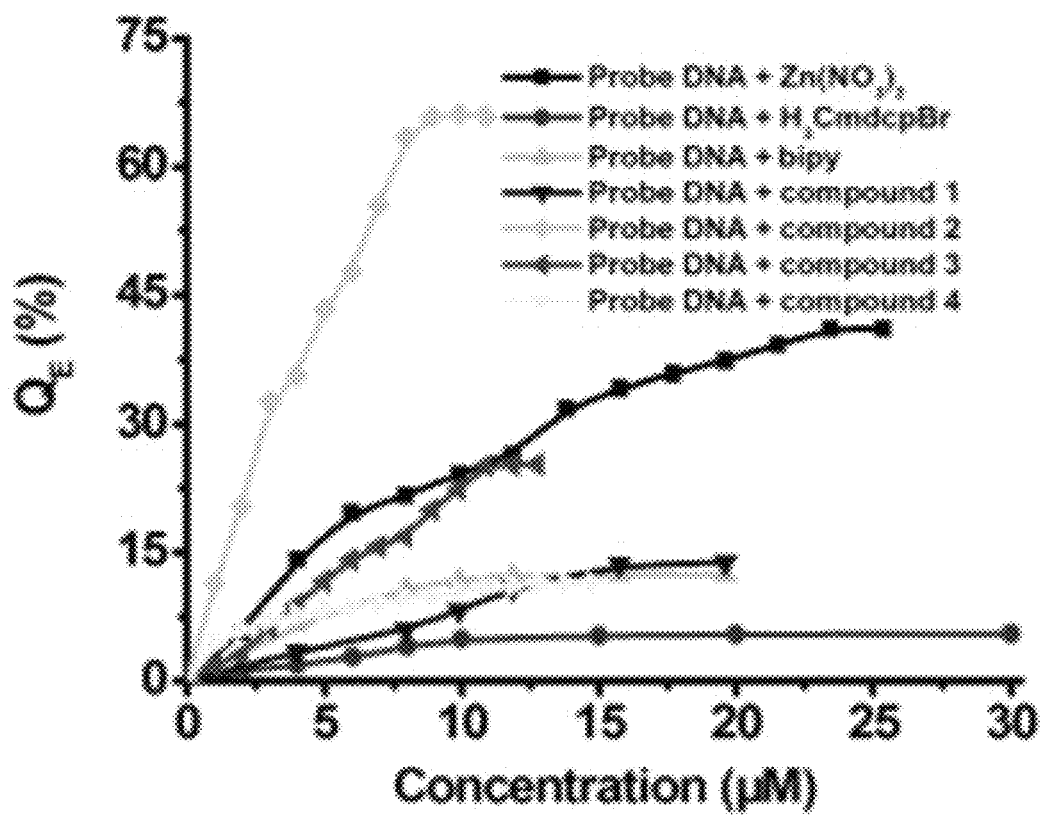
FIG. 2A is a diagram showing the fluorescence quenching efficiency of the probe DNA (70 nM) by compounds 1 to 4, $H_3CmdcpBr$ (N-carboxymethyl-(3,5-dicarboxyl) pyridinium bromide, also referred to as 3,5-dicarboxy-1-(carboxymethyl)pyridin-1-ium bromide), bipy and $Zn(NO_3)_2$ of varying concentrations at room temperature.
Figure 2B:
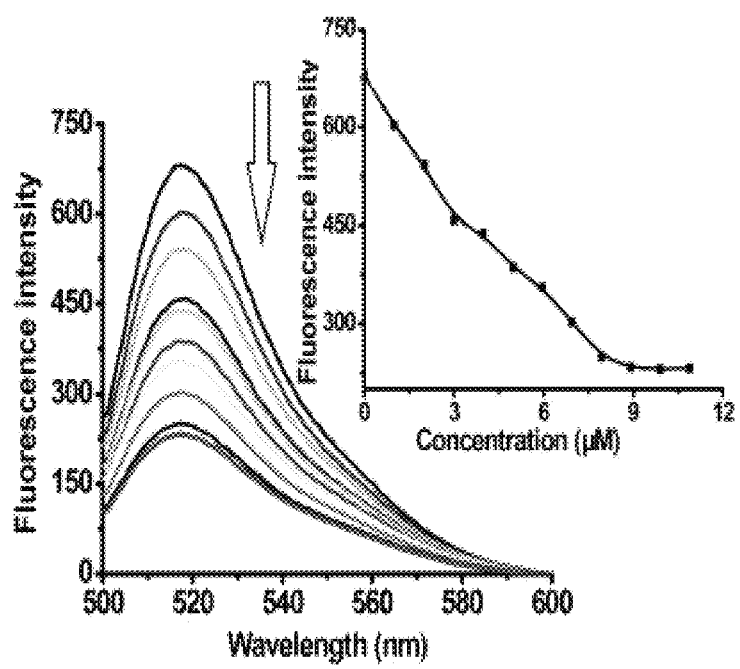
FIG. 2B shows a diagram with the fluorescence intensity of probe DNA (P-DNA, 70 nM) incubated with compound 2 of varying concentrations at room temperature (inset: plot of fluorescence intensity versus the concentrations of compound 2).

FAM-labeled ss-DNA 5'-FAM-SEQ. ID. NO:1 has been chosen as a P-DNA, which is a complementary sequence for HIV-1 ds-DNA (Chen, L. et al., Metal-organic frameworks-based biosensor for sequence-specific recognition of double-stranded DNA. Analyst. 2013; 138(12): 3490-3). As shown in FIG. 2A, the fluorescence intensity of the P-DNA decreases upon addition of compounds 1 to 4. The quenching efficiencies ($Q_E$%) are 13.8% for compound 1, 66.1% for compound 2, 25.3% for compound 3 and 11.4% for compound 4 with the saturation concentrations of 19.6 µM for compound 1, 10.9 µM for compound 2, 12.8 µM for compound 3 and 14.8 µM for compound 4, respectively. Thus, the fluorescence of P-DNA can be exceptionally quenched by compound 2 (FIG. 2B). The $Q_E$% value was calculated according to the equation $Q_E\% = (F_0 - F_M)/F_0 \times 100\%$, where $F_M$ and $F_0$ are the fluorescence intensity at 518 nm in the presence and absence of compounds 1 to 4 (Chen, L. et al., Metal-organic frameworks-based biosensor for sequence-specific recognition of double-stranded DNA. Analyst. 2013; 138(12): 3490-3).

As compound 2 consists of $Zn^{2+}$, $Cmdcp^{2-}$ and bipy that are linked through non-covalent bonds the quenching efficiencies of $H_3CmdcpBr$, bipy and $Zn(NO_3)$ have been studied to gain further insight into the quenching mechanism of compound 2. As shown in FIG. 2A, the fluorescence quench efficiencies were 5.5% for $H_3CmdcpBr$, 8.5% for bipy and 41.1% for $Zn(NO_3)_2$ with the saturation concentrations of 25.3 µM for $H_3CmdcpBr$, 8.5 µM for bipy and 10 µM for $Zn(NO_3)_2$, respectively. The results suggest that the 1D coordination polymer structure of compound 2 is highly advantageous to the fluorescence quenching, in which $Zn^{2+}$ ions play a major role. The quenching mechanism may be a consequence of the intercalation of $Zn^{2+}$ ions into the base pairs of P-DNA and the electrostatic binding with the phosphate backbones, triggering a photo-induced electron transfer (PET) process from FAM to $Zn^{2+}$ (de Silva, A. P. et al., Signaling Recognition Events with Fluorescent Sensors and Switches. Chem Rev. 1997; 97(5): 1515-66).

For compound 1, the whole 2D network is not in the same plane. Compound 3 is an ionic metal compound, while for compound 4, the dissociative aqua solvates and pbz ligands are packed closely between the 2D networks. These structural features are expected to impede the interaction between P-DNA and the compounds, i.e. it becomes more difficult for the P-DNA to effectively contact with compounds 1, 3 or 4.

When P-DNA interacts with compound 2, also referenced as "P-DNA@2 system", addition of the relevant target HIV-1 ds-DNA is expected to lead to the formation of a rigid triplex structure via reverse Hoogsteen base pairing in the major groove with P-DNA (Chen, L. et al., Metal-organic frameworks-based biosensor for sequence-specific recognition of double-stranded DNA. Analyst. 2013; 138(12): 3490-3). The formation of triplex structure is expected to keep the P-DNA away from the surface of compound 2, leading to the fluorescence regeneration. That the P-DNA@2 system can serve as sensing platform for HIV-1 ds-DNA was confirmed by the fluorescence regeneration induced by the addition of complementary HIV-1 ds-DNA ($T_0$) as target DNA.

Figure 2C:
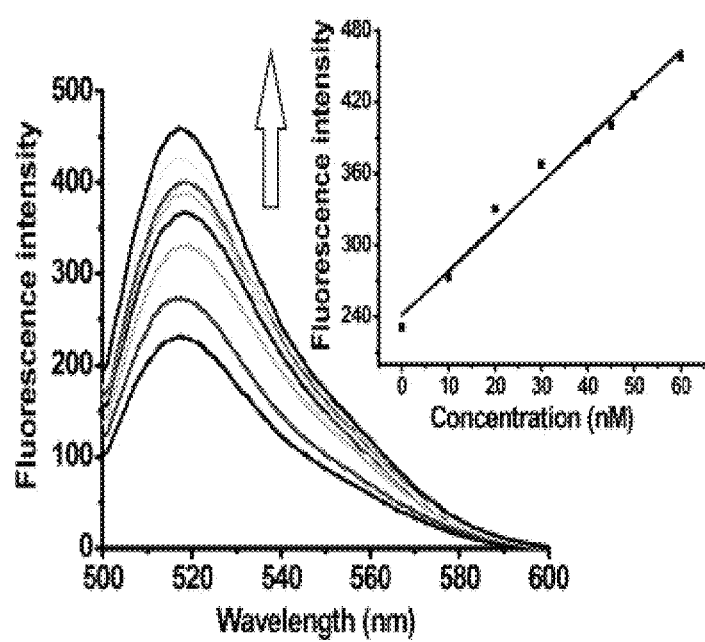
FIG. 2C is a diagram showing the fluorescence intensity of the P-DNA@2 system incubated with target HIV-1 ds-DNA of varying concentrations at room temperature (inset: plot of fluorescence intensity versus the concentrations of target HIV-1 ds-DNA in the range of 0-60 nM).
Figure 6:
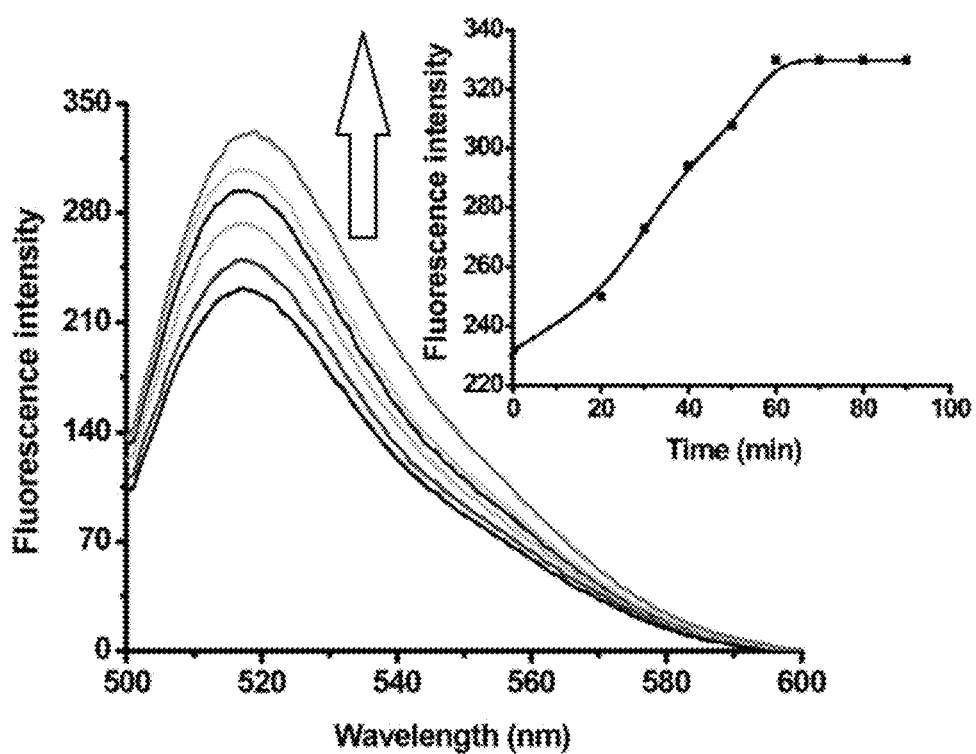
FIG. 6: Fluorescence intensity of P-DNA@2 system (70 nM/10.9 nM) in the presence of target HIV DNA $T_0$ (20 nM) and varying incubation time. Insets: plots of fluorescence intensity at 518 nm versus the incubation time for target HIV DNA $T_0$.

The results are shown in FIG. 2C and indicate that the fluorescence intensity could be recovered in the presence of target $T_0$. With the increased concentration of the target $T_0$, more P-DNAs are released, which also cause a gradual increase in the fluorescence intensity. Hence, the fluorescence intensity can be used to monitor the concentration of target HIV-1 ds-DNA. In addition, the fluorescence intensity recovery efficiency was time dependent. The fluorescence intensity increased with incubation time and remained unchanged when the incubation time was longer than 60 min with a concentration of 20 nM for $T_0$ (FIG. 6). Thus, 60 min incubation time was chosen as one of the operational conditions. Upon the addition of target HIV-1 ds-DNA, the fluorescence intensity increased gradually until saturation was observed at the concentration of 60 nM. Under this condition, the fluorescence intensity showed a good linear relationship with the concentration of target DNA (inset illustration of FIG. 2C). This gave the detection limit of 7.4 nM (S/N=3), which was calculated from $3\delta_b$/slope ($\delta_b$=standard deviation of five blank measurements).

Figure 2D:
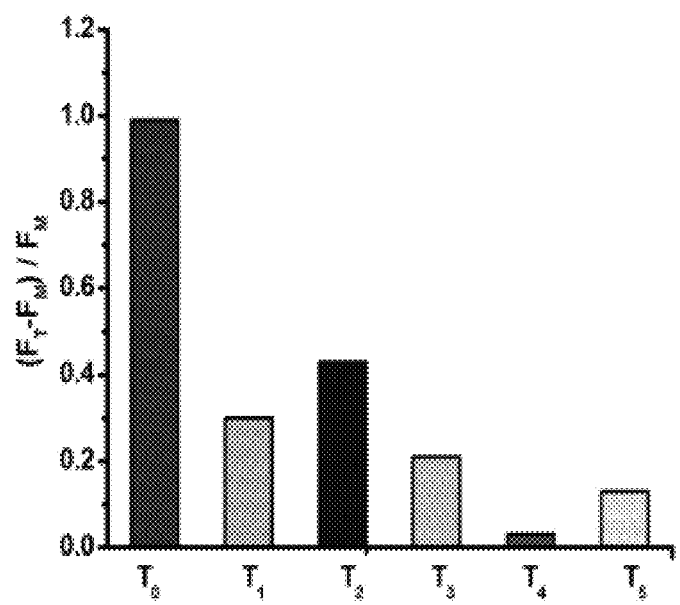
FIG. 2D shows the fluorescence intensity recovery efficiency of the P-DNA@2 system toward $T_0$ and $T_1$ to $T_5$ (60 nM).

The specificity of the sensing platform was investigated by introducing various targets. Five different targets have been chosen (one base pair mutated ds-DNA $T_1$ ($^{12}G$ and $^{41}C$ bases of $T_0$ were replaced with $^{12}A$ and $^{41}T$, respectively), the complementary ss-DNA $T_2$, one base pair mutated for complementary ss-DNA $T_3$ ($^5A$ base of $T_2$ was replaced with $^5C$), non-specific ss-DNA $T_4$ and higher-order dimeric G-quadruplex $T_5$ to hybridize with P-DNA. Upon the addition of the target $T_0$, the P-DNA is expected to have formed a rigid triplex structure via reverse Hoogsteen base pairing in the major groove resulting in significant fluorescence enhancement with the $R_E$ of 0.99, which was calculated using the formula $R_E = F_T/F_M$—wherein $F_T$ and $F_M$ are the fluorescence intensities at 518 nm in the presence and the absence of $T_0$, respectively (Chen, L. et al., Metal-organic frameworks-based biosensor for sequence-specific recognition of double-stranded DNA. Analyst. 2013; 138(12): 3490-3). While for the complementary ss-DNA $T_2$, the $R_E$ value was 0.43. At the same concentration, the fluorescence recoveries $R_E$ were 0.3 for $T_1$, 0.21 for $T_3$, 0.03 for $T_4$ and 0.12 for $T_5$, respectively (FIG. 2D). It was found that only the presence of target $T_0$ could restore the fluorescence, while the presence of other targets failed to do so.

Figure 3:
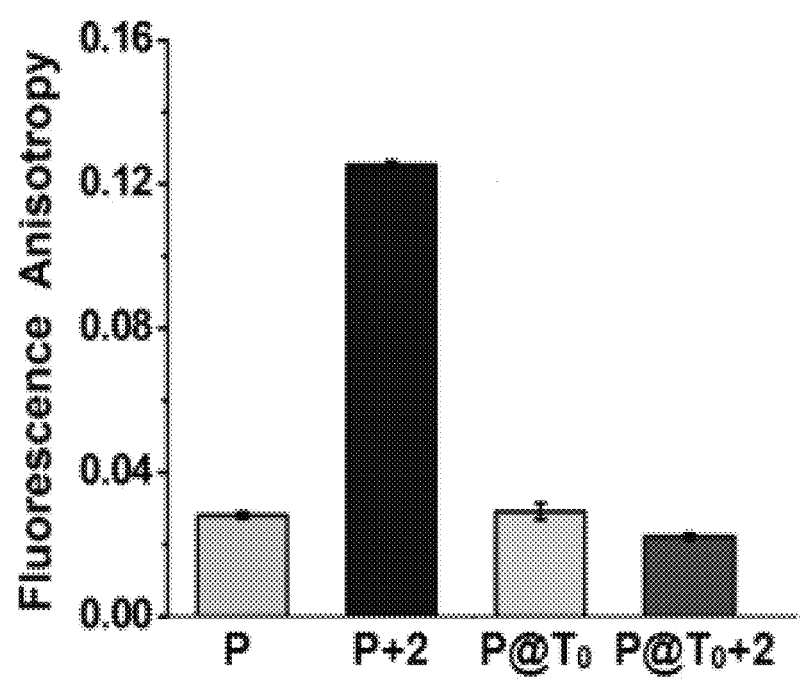
FIG. 3 shows the fluorescence anisotropy change of probe DNA (P-DNA, 70 nM) and P-DNA@$T_0$ (P@$T_0$, 70 nM/60 nM) before and after the addition of compound 2 (10.9 μM). The incubation time was 60 min for P or P@$T_0$ with compound 2.
Figure 4:
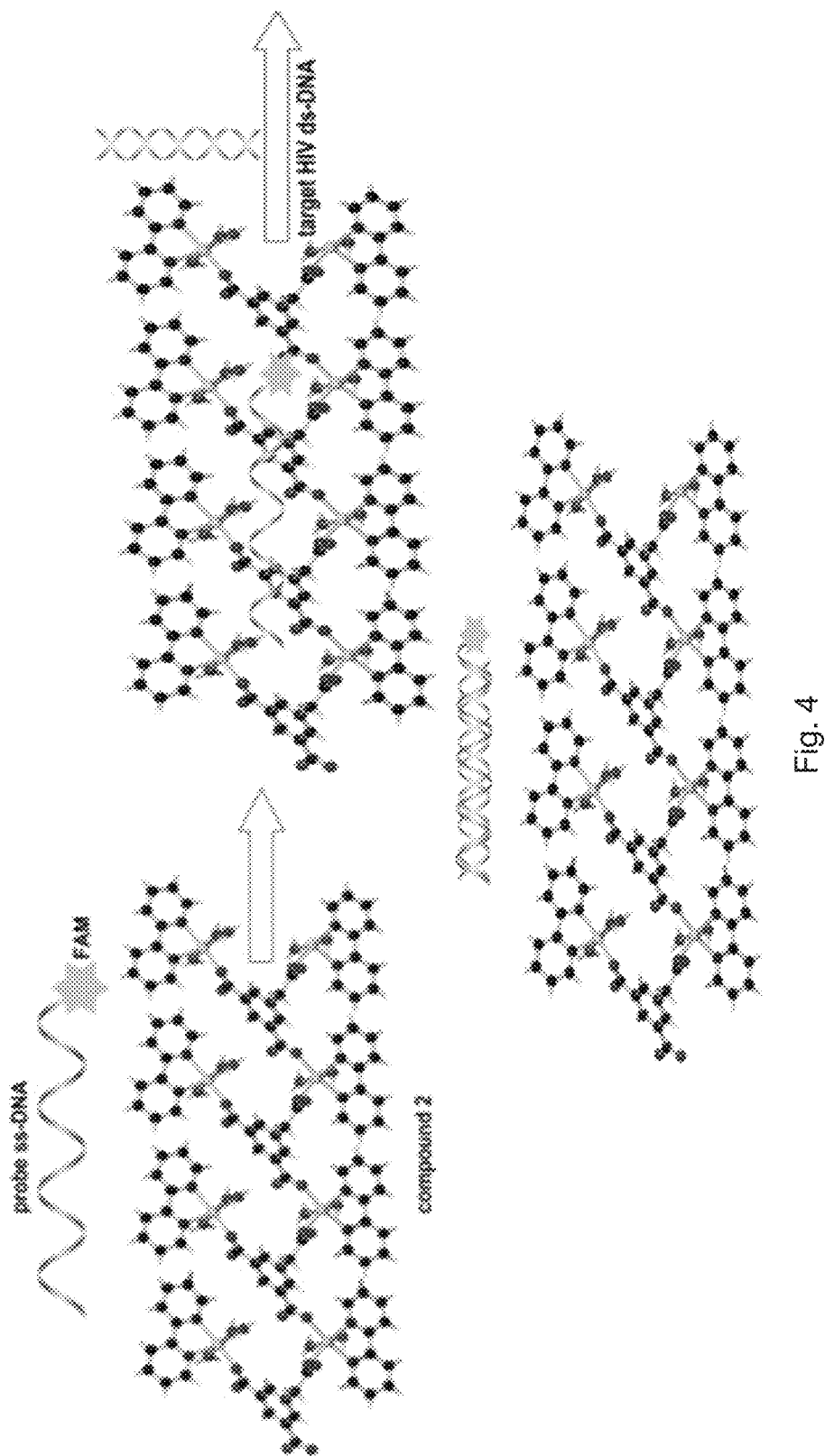
FIG. 4 illustrates the mechanism for the target HIV-1 ds-DNA detection based on the fluorescent biosensor formed from compound 2 with FAM-labeled probe ss-DNA.

These results indicate that the sensing platform of compound 2 is especially suitable for the detection of HIV-1 ds-DNA with good specificity in vitro. Thus, compound 2 proved to be able to advantageously absorb P-DNA through electrostatic, Tr-stacking interactions to form P-DNA@2 system, and thus quench the fluorescence of FAM via a PET process (FIG. 4). Compound 2 proved to have lower affinity for triplex DNA than single strand DNA which might be because of the absence of unpaired bases and the rigid conformation of triplex DNA. The flexibility of probe ss-DNA is assumed to allow close interaction with the surface of compound 2 through multiple non-covalent interactions. In the presence of target HIV-1 ds-DNA, the hybridization of target HIV-1 ds-DNA with absorbed P-DNA will alter the conformation of P-DNA. This structural alteration is expected to release P-DNA from compound 2 to form triplex DNA to the solution, which results in the recovery of fluorescence of FAM. This is supported by the changes of the fluorescence anisotropy (FA) of the P-DNA, P-DNA@target HIV ds-DNA (P@$T_0$) before and after the addition of compound 2. It is known that fluorescence anisotropy can be a measure for the rotational motion-related factors of fluorophore-labeled DNA (Liu, D. et al., Single-crystal-to-single-crystal transformation of a two-dimensional coordination polymer through highly selective [2+2] photodimerization of a conjugated dialkene. Chem Commun (Camb). 2014; 50(24): 3173-5) and thus provide a means to judge whether P-DNA and the formed P@$T_0$ (rigid triplex) are attached to the surface of compound 2. As shown in FIG. 3, the addition of compound 2 into P-DNA led to an increase in the fluorescence anisotropy by a factor of 4.4, whereas has little influence on the P@$T_0$. This result reveals the stronger interaction of compound 2 with probe ss-DNA than with rigid triplex DNA.

In summary, four water-stable zwitterionic zinc carbon/late compounds 1 to 4 have been synthesized and characterized in these examples. Among them, compound 2 proved to provide a particular advantageous and effective fluorescent sensing platform for the detection of HIV-1 ds-DNA with a detection limit of 7.4 nM and with good selectivity to the specific HIV-1 ds-DNA.

The invention claimed is:

1. A method of preparing a crystalline zwitterionic zinc(II)-carboxylate compound defined by repeating coordination entities with the formula [Zn(Cmdcp)(H$_2$O)], the method comprising the steps of:
   (i) preparing a mixture comprising zinc(II) ions and a first pyridyl ligand, said step of preparing a mixture including:
      (a) preparing a first pre-mixture comprising mixing the first pyridyl ligand and a solvent, wherein the first pyridyl ligand has a structure of Formula (III):

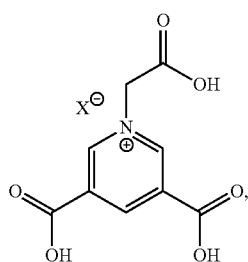

Formula (III)

wherein X is Br,
      (b) preparing a second pre-mixture comprising mixing a hydrate of Zn(NO$_3$)$_2$ and a solvent, and
      (c) adding the second pre-mixture to the first pre-mixture;
   (ii) stirring the mixture to form a precipitate;
   (iii) separating the precipitate from the mixture;
   (iv) adding a solvent to the precipitate separated in step (iii), the solvent comprising water and the solvent being added at a temperature of between 20° C. and 30° C.;
   (v) filtering the solvent and precipitate mixture of step (iv) to obtain a filtrate and a residue; and, after step (v),
   (vi) allowing the filtrate to stand and form crystals of the zwitterionic zinc(II)-carboxylate compound; and
   (vii) separating the crystals of the zwitterionic zinc(II)-carboxylate compound.

2. The method of claim 1, wherein both of the solvent in step (i)(a) and the solvent in step (1)(b) independently comprise an aliphatic alcohol.

3. The method of claim 1, wherein, in step (ii), the mixture is stirred for between 15 min and 60 min, and, in step (iii), the precipitate is separated by filtration, and wherein, prior to step (iv), the method further comprises a step of purifying the precipitate.

4. The method of claim 3, wherein the precipitate is purified by washing with a washing solvent comprising an aliphatic alcohol.

5. The method of claim 1, wherein, in step (vi), the filtrate is allowed to stand at a temperature between 20° C. and 30° C. for at least 48 hours for forming crystals of the zwitterionic zinc(II)-carboxylate compound.

6. The method of claim 1, wherein step (vii) comprises the steps of:
   a) separating the crystals from the mixture;
   b) purifying the crystals; and
   c) drying the crystals.

7. A crystalline zwitterionic zinc(II)-carboxylate compound obtained by the method of claim 1.

8. A method of preparing a crystalline zwitterionic zinc(II)-carboxylate compound defined by the formula {[Zn$_2$(Cmdcp)(bipy)$_2$(H$_2$O)$_5$](NO$_3$)$_2$.3H$_2$O}, the method comprising the steps of:
   (i) preparing a mixture comprising zinc(II) ions and a first pyridyl ligand, said step of preparing a mixture including:

(a) preparing a first pre-mixture comprising mixing the first pyridyl ligand and a solvent, wherein the first pyridyl ligand has a structure of Formula (III):

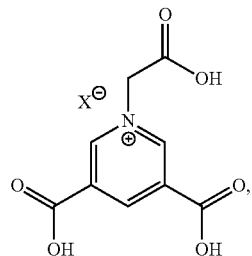

Formula (III)

wherein X is Br,
(b) preparing a second pre-mixture comprising mixing a hydrate of Zn(NO$_3$)$_2$ and a solvent, and
(c) adding the second pre-mixture to the first pre-mixture;
(ii) stirring the mixture to form a precipitate;
(iii) separating the precipitate from the mixture;
(iv) adding a solvent to the precipitate separated in step (iii), the solvent comprising water and the solvent being added at a temperature of between 20° C. and 30° C.;
(v) filtering the solvent and precipitate mixture of step (iv) to obtain a filtrate and a residue;
(vi) adding a second pyridyl ligand to the filtrate, wherein the second pyridyl ligand has a structure of Formula (IV):

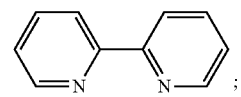

Formula (IV)

and, after step (vi),
(vii) allowing the filtrate to stand crystals of the zwitterionic zinc(II)-carboxylate compound are formed; and
(viii) separating the crystals of the zwitterionic zinc(II)-carboxylate compound.

9. The method of claim 8, wherein both of the solvent in step (i)(a) and the solvent in step (1)(b) independently comprise an aliphatic alcohol.

10. The method of claim 8, wherein, in step (ii), the mixture is stirred for between 15 min and 60 min, for forming the precipitate and, in step (iii), the precipitate is separated by filtration, and wherein, prior to step (iv), the method further comprises a step of purifying the precipitate.

11. The method of claim 10, wherein the precipitate is purified by washing with a washing solvent comprising an aliphatic alcohol.

12. The method of claim 8, wherein, in step (vii), the filtrate is allowed to stand at a temperature between 20° C. and 30° 20 C. for at least 48 hours for forming crystals of the zwitterionic zinc(II)-carboxylate compound.

13. The method of claim 8, wherein step (viii) comprises the steps of:
a) separating the crystals from the mixture;
b) purifying the crystals; and
c) drying the crystals.

14. A crystalline zwitterionic zinc(II)-carboxylate compound obtained by the method of claim 8.

* * * * *